US007807848B2

(12) United States Patent
Wang

(10) Patent No.: US 7,807,848 B2
(45) Date of Patent: Oct. 5, 2010

(54) REDUCTION OF STEROLS AND OTHER COMPOUNDS FROM OILS

(75) Inventor: Weijie Wang, Dartmouth (CA)

(73) Assignee: Ocean Nutrition Canada Limited, Dartmouth, Nova Scotia (CA)

( * ) Notice: Subject to any disclaimer, the term of this patent is extended or adjusted under 35 U.S.C. 154(b) by 0 days.

(21) Appl. No.: 11/991,021

(22) PCT Filed: Aug. 25, 2006

(86) PCT No.: PCT/IB2006/004059
§ 371 (c)(1),
(2), (4) Date: Nov. 4, 2008

(87) PCT Pub. No.: WO2007/088421
PCT Pub. Date: Aug. 9, 2007

(65) Prior Publication Data
US 2009/0118525 A1    May 7, 2009

Related U.S. Application Data

(60) Provisional application No. 60/712,029, filed on Aug. 26, 2005.

(51) Int. Cl.
*C11B 3/00*        (2006.01)
(52) U.S. Cl. .................................................. 554/191
(58) Field of Classification Search .................. 554/191
See application file for complete search history.

(56) References Cited

U.S. PATENT DOCUMENTS

| | | | |
|---|---|---|---|
| 4,298,622 | A | 11/1981 | Singh et al. |
| 4,349,451 | A | 9/1982 | Friedman .................. 252/190 |
| 4,554,107 | A | 11/1985 | Takao ....................... 260/421 |
| 4,623,488 | A | 11/1986 | Takao ..................... 260/410.7 |
| 4,681,768 | A | 7/1987 | Mulfur et al. ............... 426/417 |
| 4,764,392 | A | 8/1988 | Yasufuku et al. ............ 426/603 |
| 4,804,555 | A | 2/1989 | Marschner et al. .......... 426/601 |
| 4,874,629 | A * | 10/1989 | Chang et al. ................ 426/601 |
| 4,996,072 | A | 2/1991 | Marschner et al. .......... 426/417 |
| 5,023,100 | A | 6/1991 | Chang et al. ................ 426/601 |
| 5,091,117 | A * | 2/1992 | Athnasios et al. ........... 554/193 |
| 5,128,162 | A * | 7/1992 | Wrezel et al. ............... 426/417 |
| 5,155,245 | A | 10/1992 | Myojo et al. ................ 552/545 |
| 5,171,177 | A | 12/1992 | Hubbell ...................... 440/78 |
| 6,469,187 | B1 | 10/2002 | Craven et al. ............... 554/195 |
| 6,623,774 | B2 | 9/2003 | Kendrick et al. .......... 426/330.6 |
| 7,179,491 | B1 | 2/2007 | Mag ........................... 424/522 |
| 2003/0161918 | A1 | 8/2003 | Kendrick |
| 2003/0193102 | A1 | 10/2003 | Yan ............................ 264/4.1 |
| 2004/0210070 | A1 | 10/2004 | Kruidenberg ............... 554/205 |

FOREIGN PATENT DOCUMENTS

| | | |
|---|---|---|
| CA | 2136018 | 9/1994 |
| CN | 1098874 | 2/1995 |
| EP | 442184 | 8/1991 |
| JP | 62-145099 | 6/1987 |
| JP | 41-68198 | 6/1992 |
| JP | 42-02599 | 7/1992 |
| JP | 51-71177 | 7/1993 |
| JP | 83-11482 | 11/1996 |
| JP | 92-96198 | 11/1997 |
| WO | WO 95/24459 | 9/1995 |
| WO | WO 96/08547 | 3/1996 |
| WO | WO 00/44862 | 8/2000 |
| WO | WO 2004/007654 | 1/2004 |
| WO | WO 2004/007655 | 1/2004 |
| WO | WO 2004/041251 | 5/2004 |

OTHER PUBLICATIONS

Ackman, "Marine Biogenic Lipids, Fats, and Oils," CRC Press, Inc. Boca Raton, Florida, vol. 2, pp. 401-433 (1989).
Ackman, "Fish Oils" Bailey's Industrial Oil and Fat Products, Sixth Ed., John Wiley & Sons, Inc. (2005).
Appel et al., "Does supplementation of diet with 'fish oil' reduce blood pressure? A meta-analysis of controlled clinical trials," *Arch Intern Med*, 153(12):1429-1438 (1993).
Bimbo, "Guidelines for characterizing food-grade fish oil," *INFORM*, 9(5):473-481 (1998).
Čmolík et al., "Physical refining of edible oils," *Eur J Lipid Sci Technol*, 102:472-486 (2000).
Davison, "Simplification of the refining process using TriSyl® silicas," http:www.gracedavison.com/products/fcph/trisyl/refining.htm (1999).
Davison, "Simplification of the refining process using TriSyl® silicas," http:www.gracedavison.com/products/fcph/trisyl/overview.htm (1999).
Dyrberg et al., "In: Omega-3 fatty acids: prevention and treatment of vascular disease," Kristensen et al., Eds., Bi & Gi Publ., Verona-Springer-Verlag, London, pp. 217-226 (1995).
El-Hassan et al., "A process for high yield and scaleable recovery of high purity eicosapentaenoic acid esters from microalgae and fish oil," *Process Biochem*, 35:951-969 (2000).
Gauglitz et al., "Adsorptive bleaching and molecular distillation of menhaden oil," *J Am Oil Chem Soc*, 42:561-563 (1965).
GISSI-Prevenzione Investigators, "Dietary supplementation with omega-3 polyunsaturated fatty acids and vitamin E after myocardial infarction: results of the GISSI-Prevenzione trial," *Lancet*, 354:447-55 (1999).
International Search Report and Written Opinion of PCT/IB2006/004059 mailed Oct. 5, 2007.

(Continued)

*Primary Examiner*—Deborah D Carr
(74) *Attorney, Agent, or Firm*—McKeon Meunier Carlin Curfman

(57) ABSTRACT

Disclosed are methods of removing and/or reducing compounds from oils (e.g., marine oils) and oils prepared by the disclosed methods. Methods of bleaching oils are also disclosed.

16 Claims, No Drawings

OTHER PUBLICATIONS

International Preliminary Report on Patentability for PCT/IB2006/004059 mailed Mar. 6, 2008.

Joseph, "Biomedical Test Materials Program: Production Methods and Safety Manual," NOAA Technical Memorandum NMFS SEFC, U.S. Dept. of Commerce (1989).

Kawashima et al., "Experimental study on the removal of dioxins and coplanar polychlorinated biphenyls (PCBs) from fish oils," *J Agri Food Chem*, 54:10294-10299 (2006).

Kris-Etherton et al., "Fish consumption, fish oil, Omega-3 fatty acids and cardiovascular disease," The American Heart Association Scientific Statement, 106(21):2747-57, Nov. 2002.

O'Keefe and Harris, "Omega-3 fatty acids: Time for clinical implementation?" *Am J Cardiology*, 85:1239-1241 (2000).

Radack et al., "The effects of low doses of omega-3 fatty acid supplementation on blood pressure in hypertensive subjects: a randomized controlled trial," *Arch Intern Med*, 151:1173-1180 (1991).

Proceeding in Peruvian Application No. 001004-2006; Notice of Opposition filed Sep. 3, 2007, and Response to Notice of Opposition filed Oct. 13, 2007 (English translations).

Sugano and Michihiro, "Balanced intake of polyunsaturated fatty acids for health benefits," *J Oleo Sci*, 50(5):305-311 (2001).

Office Action for CN200680039104.7 dated Nov. 27, 2009.

Office Action for AU2006337417 dated Jan. 29, 2010.

Office Action for PE 001004-2006 dated Aug. 5, 2009.

Supplemental European Search Report for EP06849452.5 dated May 12, 2010.

\* cited by examiner

REDUCTION OF STEROLS AND OTHER COMPOUNDS FROM OILS

CROSS REFERENCE TO RELATED APPLICATIONS

This application claims the benefit of priority to U.S. Provisional Application No. 60/712,029, filed on Aug. 26, 2005, which is incorporated by reference herein in its entirety.

FIELD

The disclosed matter relates to methods of removing and/or reducing compounds from oils (e.g., marine oils) and to oils prepared by the disclosed methods. Methods of bleaching oils are also disclosed.

BACKGROUND

Polyunsaturated fatty acids (PUFA) such as the omega-3 fatty acids are vital to everyday life and function. For example, the beneficial effects of omega-3 fatty acids like cis-5,8,11,14,17-eicosapentaenoic acid (EPA) and cis-4,7,10,13,16,19-docosahexaenoic acid (DHA) on lowering serum triglycerides are now well established. These compounds are also known for other cardioprotective benefits. See e.g., Dyrberg, et al., In: ω-3 Fatty Acids: Prevention and Treatment of Vascular Disease. Kristensen, et al., eds., Bi & Gi Publ., Verona-Springer-Verlag, London, pp. 217-26, 1995; O'Keefe and Harris, *Am. J. Cardiology* 2000, 85: 1239-41; Radack et al., "The effects of low doses of omega-3 fatty acid supplementation on blood pressure in hypertensive subjects: a randomized controlled trial." *Arch. Intern. Med.* 1991, 151: 1173-1180. Indeed, the American Heart Association has also reported that omega-3 fatty acids can reduce cardiovascular and heart disease risk. Other benefits of PUFAs are those related to the prevention and/or treatment of inflammation, neurogenerative diseases, and cognitive development. See e.g., Sugano, Michihiro, "Balanced intake of polyunsaturated fatty acids for health benefits." *J. Oleo Sci.* 2001, 50(5): 305-311.

A primary source of many polyunsaturated fatty acids, including omega-3 fatty acids, is fish oil. Diets rich in fish oils are known to have many beneficial effects for heart disease, cancer, arthritis, allergies, and other chronic diseases. (See e.g., The American Heart Association, Scientific Statement, "Fish Consumption, Fish Oil, Omega-3 Fatty Acids and Cardiovascular Disease," November 2002; Appel et al., "Does supplementation of diet with 'fish oil' reduce blood pressure? A meta-analysis of controlled clinical trials." *Arch. Intern. Med.* 1993, 153(12):1429-1438; GISSI-Prevenzione Investigators. "Dietary supplementation with omega-3 polyunsaturated fatty acids and vitamin E after myocardial infarction: results of the GISSI-Prevenzione trial." *Lancet* 1999, 354: 447-455.)

Some fish oils can contain compounds that may be undesirable for a particular purpose. As such, various methods have been tried in order to remove and/or reduce undesirable compounds from fish oils. For example, distillation has been tried to reduce cholesterol from fish oils but such methods usually require extreme temperature and pressure. Moreover, distillation can produce dark oil and can adversely affect the taste of the oil. Also, distillation can be costly on a commercial scale, and yields are often poor. Other methods involving chemical extractions and/or transformations have also been tried but the expense of reagents and contamination from the chemical extractants, solvents, and reactants can be problematic.

In light of the problems associated with removing undesirable compounds from fish oils, what is needed in the art are methods for removing and/or reducing various compounds from oils. Also needed are oils prepared from such methods (e.g., oils with reduced levels of various undesirable compounds). The subject matter disclosed herein meets these and other needs.

SUMMARY

In accordance with the purposes of the disclosed materials, compounds, compositions, articles, and methods, as embodied and broadly described herein, the disclosed subject matter, in one aspect, relates to compositions and methods for preparing and using such compositions. In a further aspect, the disclosed subject matter relates to methods of removing compounds (e.g., sterols) from compositions such as marine oils. In still a further aspect, the disclosed subject matter relates to methods of bleaching compositions. Still further, the disclosed subject matter relates to compositions prepared by the methods disclosed herein.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, articles, and methods described herein may be understood more readily by reference to the following detailed description of specific aspects of the disclosed subject matter and the Examples included therein.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an adsorbent" includes mixtures of two or more such adsorbents, reference to "the oil" includes mixtures of two or more such oils, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data is provided in a number of different formats and that this data represents endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular component in a composition denotes the weight relationship between the component and any other components in the composition for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

Reference will now be made in detail to specific aspects of the disclosed materials, compounds, compositions, articles, and methods, examples of which are illustrated in the accompanying Examples.

Materials and Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of components or residues of the compound are discussed, each and every combination and permutation that are possible are specifically contemplated unless specifically indicated to the contrary. Thus, if a class of components A, B, and C are disclosed as well as a class of components D, E, and F and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Disclosed herein, in one aspect, are compositions that are oils. In many examples, the compositions are derived from marine oils. Marine oils, as used herein, refer to oils that are isolated from marine life. For example, marine oils can be oils that are isolated from fish, Mollusca such as squid, cuttle fish, and/or octopus, Crustacea such as krill, and marine mammals such as seals and whales. Specific examples of suitable marine oils include, but are not limited to, Atlantic fish oils, Pacific fish oils, Mediterranean fish oils, light pressed fish oil, alkaline treated fish oil, heat treated fish oil, light and heavy brown fish oil, tuna oil, bonito oil, sea bass oil, halibut oil, spearfish oil, barracuda oil, cod oil, menhaden oil, sardine oil, pilchard oil, anchovy oil, capelin oil, Atlantic cod oil, Atlantic herring oil, Atlantic mackerel oil, Atlantic menhaden oil, salmonids oil, shark oil, squid oil, octopus oil, krill oil, seal oil, whale oil, and the like, including mixtures and combinations thereof. Any marine oil and combination of marine oil can be used in the disclosed compositions and methods. In other examples, the compositions can be oils that are isolated from vegetables and plants, animals, and microbes, as well as edible oils. Further examples of suitable oils include crude oils from such sources disclosed herein as well as semi-refined (also called alkaline refined) and refined oils from such sources. Still further, the disclosed compositions and methods can use oils comprising re-esterified triglycerides. Also, any combination of these oils can be used.

The disclosed compositions can be prepared by methods described herein. For example, the disclosed methods can be used to reduce and/or remove various compounds from oils to provide the disclosed compositions. As one specific example, the disclosed compositions can be marine oils that have been treated according to the disclosed methods and comprise reduced levels of compounds such as sterols, as compared to the original oil. In other examples, the disclosed compositions can be plant, animals, microbe, edible, crude, semi-refined, refined, and/or re-esterified oils that have been treated according to the disclosed methods, which comprise reduced levels of compounds such as sterols as compared to the starting oil.

Levels of Sterols

In many examples, the disclosed compositions contain reduced levels of sterols (e.g., cholesterol) as compared to a starting oil. By starting oil is meant any oil before it has been treated according to the methods disclosed herein. A suitable starting oil can be any oil as disclosed herein, for example, oils isolated from marine life, plant life, animal life, microbes, edible oils, as well as crude oils and such oils that have been semi-refined, refined, and/or re-esterified.

The sterols that can be present at reduced levels in the disclosed compositions or that are removed from the disclosed compositions, as compared to a starting oil, can be cholesterols (e.g., free cholesterol and esterified cholesterol) and phytosterols.

In specific examples, the disclosed compositions can comprise less than or equal to about 6.0 milligrams of sterol per gram of the composition. Also, disclosed are compositions that can comprise less than or equal to about 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, or 0.0 milligrams of sterol per gram of the composition, where any of the stated values can form an upper and/or lower endpoint as appropriate. In other examples, the disclosed compositions can comprise less than about 2.5, more specifically less than about 2.0 milligrams of sterol per gram of the composition.

The disclosed compositions, in further examples, can comprise from about 6.0 to about 1.0, from about 6.0 to about 0.8, from about 6.0 to about 0.6, from about 6.0 to about 0.4, from about 6.0 to about 0.2, from about 6.0 to about 0.0, from about 5.8 to about 1.0, from about 5.8 to about 0.8, from about 5.8 to about 0.6, from about 5.8 to about 0.4, from about 5.8 to about 0.2, from about 5.8 to about 0.0, from about 5.6 to about 1.0, from about 5.6 to about 0.8, from about 5.6 to about 0.6, from about 5.6 to about 0.4, from about 5.6 to about 0.2, from about 5.6 to about 0.0, from about 5.4 to about 1.0, from about 5.4 to about 0.8, from about 5.4 to about 0.6, from about 5.4 to about 0.4, from about 5.4 to about 0.2, from about 5.4 to about 0.0, from about 5.2 to about 1.0, from about 5.2 to about 0.8, from about 5.2 to about 0.6, from about 5.2 to about 0.4, from about 5.2 to about 0.2, from about 5.2 to about 0.0, from about 5.0 to about 1.0, from about 5.0 to about 0.8, from about 5.0 to about 0.6, from about 5.0 to about 0.4, from about 5.0 to about 0.2, from about 5.0 to about 0.0, from about 4.8 to about 1.0, from about 4.8 to about 0.8, from about 4.8 to about 0.6, from about 4.8 to about 0.4, from about 4.8 to about 0.2, from about 4.8 to about 0.0, from about 4.6 to about 1.0, from about 4.6 to about 0.8, from about 4.6 to about 0.6, from about 4.6 to about 0.4, from about 4.6 to about 0.2, from about 4.6 to about 0.0, from about 4.4 to about 1.0, from about 4.4 to about 0.8, from about 4.4 to about 0.6, from about 4.4 to about 0.4, from about 4.4 to about 0.2, from about 4.4 to about 0.0, from about 4.2 to about 1.0, from about 4.2 to about 0.8, from about 4.2 to about 0.6, from about 4.2 to about 0.4, from about 4.2 to about 0.2, from about 4.2 to about 0.0, from about 4.0 to about 1.0, from about 4.0 to about 0.8, from about 4.0 to about 0.6, from about 4.0 to about 0.4, from about 4.0 to about 0.2, from about 4.0 to about 0.0, from about 3.8 to about 1.0, from about 3.8 to about 0.8, from about 3.8 to about 0.6, from about 3.8 to about 0.4, from about 3.8 to about 0.2, from about 3.8 to about 0.0, from about 3.6 to about 1.0, from about 3.6 to about 0.8, from about 3.6 to about 0.6, from about 3.6 to about 0.4, from about 3.6 to about 0.2, from about 3.6 to about 0.0, from about 3.4 to about 1.0, from about 3.4 to about 0.8, from about 3.4 to about 0.6, from about 3.4 to about 0.4, from about 3.4 to about 0.2, from about 3.4 to about 0.0, from about 3.2 to about 1.0, from about 3.2 to about 0.8, from about 3.2 to about 0.6, from about 3.2 to about 0.4, from about 3.2 to about 0.2, from about 3.2 to about 0.0, from about 3.0 to about 1.0, from about 3.0 to about 0.8, from about 3.0 to about 0.6, from about 3.0 to about 0.4, from about 3.0 to about 0.2, from about 3.0 to about 0.0, from about 2.8 to about 1.0, from about 2.8 to about 0.8, from about 2.8 to about 0.6, from about 2.8 to about 0.4, from about 2.8 to about 0.2, from about 2.8 to about 0.0, from about 2.6 to about 1.0, from about 2.6 to about 0.8, from about 2.6 to about 0.6, from about 2.6 to about 0.4, from about 2.6 to about 0.2, from about 2.6 to about 0.0, from about 2.4 to about 1.0, from about 2.4 to about 0.8, from about 2.4 to about 0.6, from about 2.4 to about 0.4, from about 2.4 to about 0.2, from about 2.4 to about 0.0, from about 2.2 to about 1.0, from about 2.2 to about 0.8, from about 2.2 to about 0.6, from about 2.2 to about 0.4, from about 2.2 to about 0.2, from about 2.2 to about 0.0, from about 2.0 to about 1.0, from about 2.0 to about 0.8, from about 2.0 to about 0.6, from about 2.0 to about 0.4, from about 2.0 to about 0.2, from about 2.0 to about 0.0, from about 1.8 to about 1.0, from about 1.8 to about 0.8, from about 1.8 to about 0.6, from about 1.8 to about 0.4, from about 1.8 to about 0.2, from about 1.8 to about 0.0, from about 1.6 to about 1.0, from about 1.6 to about 0.8, from about 1.6 to about 0.6, from about 1.6 to about 0.4, from about 1.6 to about 0.2, from about 1.6 to about 0.0, from about 1.4 to about 1.0, from about 1.4 to about 0.8, from about 1.4 to about 0.6, from about 1.4 to about 0.4, from about 1.4 to about 0.2, from about 1.4 to about 0.0, from about 1.2 to about 1.0, from about 1.2 to about 0.8, from about 1.2 to about 0.6, from about 1.2 to about 0.4, from about 1.2 to about 0.2, from about 1.2 to about 0.0, from about 1.0 to about 0.8, from about 1.0 to about 0.6, from about 1.0 to about 0.4, from about 1.0 to about 0.2, or from about 1.0 to about 0.0 milligrams of sterol per gram of the composition.

In still other examples, the disclosed compositions can comprise from about 6.0 to about 2.0, from about 6.0 to about 1.7, from about 6.0 to about 1.5, from about 6.0 to about 1.3, from about 5.8 to about 2.0, from about 5.8 to about 1.7, from about 5.8 to about 1.5, from about 5.8 to about 1.3, from about 5.6 to about 2.0, from about 5.6 to about 1.7, from about 5.6 to about 1.5, from about 5.6 to about 1.3, from about 5.4 to about 2.0, from about 5.4 to about 1.7, from about 5.4 to about 1.5, from about 5.4 to about 1.3, from about 5.2 to about 2.0, from about 5.2 to about 1.7, from about 5.2 to about 1.5, from about 5.2 to about 1.3, from about 5.0 to about 2.0, from about 5.0 to about 1.7, from about 5.0 to about 1.5, from about 5.0 to about 1.3, from about 4.8 to about 2.0, from about 4.8 to about 1.7, from about 4.8 to about 1.5, from about 4.8 to about 1.3, from about 4.6 to about 2.0, from about 4.6 to about 1.7, from about 4.6 to about 1.5, from about 4.6 to about 1.3, from about 4.4 to about 2.0, from about 4.4 to about 1.7, from about 4.4 to about 1.5, from about 4.4 to about 1.3, from about 4.2 to about 2.0, from about 4.2 to about 1.7, from about 4.2 to about 1.5, from about 4.2 to about 1.3, from about 4.0 to about 2.0, from about 4.0 to about 1.7, from about 4.0 to about 1.5, from about 4.0 to about 1.3, from about 3.8 to about 2.0, from about 3.8 to about 1.7, from about 3.8 to about 1.5, from about 3.8 to about 1.3, from about 3.6 to about 2.0, from about 3.6 to about 1.7, from about 3.6 to about 1.5, from about 3.6 to about 1.3, from about 3.4 to about 2.0, from about 3.4 to about 1.7, from about 3.4 to about 1.5, from about 3.4 to about 1.3, from about 3.2 to about 2.0, from about 3.2 to about 1.7, from about 3.2 to about 1.5, from about 3.2 to about 1.3, from about 3.0 to about 2.0, from about 3.0 to about 1.7, from about 3.0 to about 1.5, from about 3.0 to about 1.3, from about 2.8 to about 2.0, from about 2.8 to about 1.7, from about 2.8 to about 1.5, from about 2.8 to about 1.3, from about 2.6 to about 2.0, from about 2.6 to about 1.7, from about 2.6 to about 1.5, from about 2.6 to about 1.3, from about 2.4 to about 2.0, from about 2.4 to about 1.7; from about 2.4 to about 1.5, from about 2.4 to about 1.3, from about 2.2 to about 2.0, from about 2.2 to about 1.7, from about 2.2 to about 1.5, from about 2.2 to about 1.3, from about 2.0 to about 1.7, from about 2.0 to about 1.5, or from about 2.0 to about 1.3 milligrams of sterol per gram of the composition.

In yet other examples, the disclosed compositions can comprise from about 6.0 to about 3.0, from about 6.0 to about 2.8, from about 6.0 to about 2.6, from about 6.0 to about 2.4, from about 6.0 to about 2.2, from about 5.8 to about 3.0, from about 5.8 to about 2.8, from about 5.8 to about 2.6, from about 5.8 to about 2.4, from about 5.8 to about 2.2, from about 5.6 to about 3.0, from about 5.6 to about 2.8, from about 5.6 to about 2.6, from about 5.6 to about 2.4, from about 5.6 to about 2.2, from about 5.4 to about 3.0, from about 5.4 to about 2.8, from about 5.4 to about 2.6, from about 5.4 to about 2.4, from about 5.4 to about 2.2, from about 5.2 to about 3.0, from about 5.2 to about 2.8, from about 5.2 to about 2.6, from about 5.2 to about 2.4, from about 5.2 to about 2.2, from about 5.0 to about 3.0, from about 5.0 to about 2.8, from about 5.0 to about 2.6, from about 5.0 to about 2.4, from about 5.0 to about 2.2, from about 4.8 to about 3.0, from about 4.8 to about 2.8, from about 4.8 to about 2.6, from about 4.8 to about 2.4, from about 4.8 to about 2.2, from about 4.6 to about 3.0, from about 4.6 to about 2.8, from about 4.6 to about 2.6, from about 4.6 to about 2.4, from about 4.6 to about 2.2, from about 4.4 to about 3.0, from about 4.4 to about 2.8, from about 4.4 to about 2.6, from about 4.4 to about 2.4, from about 4.4 to about 2.2, from about 4.2 to about 3.0, from about 4.2 to about 2.8, from about 4.2 to about 2.6, from about 4.2 to about 2.4, from about 4.2 to about 2.2, from about 4.0 to about 3.0, from about 4.0 to about 2.8, from about 4.0 to about 2.6, from about 4.0 to about 2.4, from about 4.0 to about 2.2, from about 3.8 to about 3.0, from about 3.8 to about 2.8, from about 3.8 to about 2.6, from about 3.8 to about 2.4, from about 3.8 to about 2.2, from about 3.6 to about 3.0, from about 3.6 to about 2.8, from about 3.6 to about 2.6, from about 3.6 to about 2.4, from about 3.6 to about 2.2, from about 3.4 to about 3.0, from about 3.4 to about 2.8, from about 3.4 to about 2.6, from about 3.4 to about 2.4, from about 3.4 to about 2.2, from about 3.2 to about 3.0, from about 3.2 to about 2.8, from about 3.2 to about 2.6, from about 3.2 to about 2.4, from about 3.2 to about 2.2, from about 3.0 to about 2.8, from about 3.0 to about 2.6, from about 3.0 to about 2.4, of from about 3.0 to about 2.2 milligrams of sterol per gram of the composition.

In a particular example, the amount of sterol in the disclosed composition can be from about 1.2 to about 0.8, from about 1.1 to about 0.9, or about 1.0 milligrams per gram of the composition.

Color

The disclosed compositions can also be lighter in color that crude oil, even crude oil that has been subjected to a bleaching procedure. Colors for the disclosed compositions and crude oils can be defined by their Gardner color. Gardner color is a color measurement based on the chromaticities of glass standards numbered from 1 for the lightest to 18 for the darkest. Gardner color measurements are well known and can involve an apparatus known as a comparator, such as the Comparator 3000 from Tintometer Ltd. (United Kingdom). Methods for measuring the Gardner color of the disclosed compositions are disclosed in ASTM D 1544; this method is available from ASTM International and is incorporated by reference herein in its entirety.

In some specific examples, the disclosed compositions can have a Gardner color of less than or equal to about 18. In other examples, the compositions disclosed herein can have a Gardner color of less than or equal to about 18, 17, 16, 15, 14, 13, 12, 11, 10, 9, 8, 7, 6, 5, 4, 3, 2, or 1 as determined by ASTM D 1544, where any of the stated values can form an upper and/or lower endpoint as appropriate.

In other examples of the disclosed compositions, the Gardner color can be from about 18 to about 1, from about 17 to about 1, from about 16 to about 1, from about 15 to about 1, from about 14 to about 1, from about 13 to about 1, from about 12 to about 1, from about 11 to about 1, from about 10 to about 1, from about 9 to about 1, from about 8 to about 1, from about 7 to about 1, from about 6 to about 1, from about 5 to about 1, from about 4 to about 1, from about 3 to about 1, from about 2 to about 1, from about 18 to about 2, from about 17 to about 2, from about 16 to about 2, from about 15 to about 2, from about 14 to about 2, from about 13 to about 2, from about 12 to about 2, from about 11 to about 2, from about 10 to about 2, from about 9 to about 2, from about 8 to about 2, from about 7 to about 2, from about 6 to about 2, from about 5 to about 2, from about 4 to about 2, from about 3 to about 2, from about 18 to about 3, from about 17 to about 3, from about 16 to about 3, from about 15 to about 3, from about 14 to about 3, from about 13 to about 3, from about 12 to about 3, from about 11 to about 3, from about 10 to about 3, from about 9 to about 3, from about 8 to about 3, from about 7 to about 3, from about 6 to about 3, from about 5 to about 3, from about 4 to about 3, from about 18 to about 4, from about 17 to about 4, from about 16 to about 4, from about 15 to about 4, from about 14 to about 4, from about 13 to about 4, from about 12 to about 4, from about 11 to about 4, from about 10 to about 4, from about 9 to about 4, from about 8 to about 4, from about 7 to about 4, from about 6 to about 4, from about 5 to about 4, from about 18 to about 5, from about 17 to about 5, from about 16 to about 5, from about 15 to about 5, from about 14 to about 5, from about 13 to about 5, from about 12 to about 5, from about 11 to, about 5, from about 10 to about 5, from about 9 to about 5, from about 8 to about 5, from about 7 to about 5, from about 6 to about 5, from about 18 to about 6, from about 17 to about 6, from about 16 to about 6, from about 15 to about 6, from about 14 to about 6, from about 13 to about 6, from about 12 to about 6, from about 11 to about 6, from about 10 to about 6, from about 9 to about 6, from about 8 to about 6, from about 7 to about 6, from about 18 to about 7, from about 17 to about 7, from about 16 to about 7, from about 15 to about 7, from about 14 to about 7, from about 13 to about 7, from about 12 to about 7, from about 11 to about 7, from about 10 to about 7, from about 9 to about 7, from about 8 to about 7, from about 18 to about 8, from about 17 to about 8, from about 16 to about 8, from about 15 to about 8, from about 14 to about 8, from about 13 to about 8, from about 12 to about 8, from about 11 to about 8, from about 10 to about 8, from about 9 to about 8, from about 18 to about 9, from about 17 to about 9, from about 16 to about 9, from about 15 to about 9, from about 14 to about 9, from about 13 to about 9, from about 12 to about 9, from about 11 to about 9, from about 10 to about 9, from about 18 to about 10, from about 17 to about 10, from about 16 to about 10, from about 15 to about 10, from about 14 to about 10, from about 13 to about 10, from about 12 to about 10, from about 11 to about 10, from about 18 to about 11, from about 17 to about 11, from about 16 to about 11, from about 15 to about 11, from about 14 to about 11, from about 13 to about 11, from about 12 to about 11, from about 18 to about 12, from about 17 to about 12, from about 16 to about 12, from about 15 to about 12, from about 14 to about 12, from about 13 to about 12, from about 18 to about 13, from about 17 to about 13, from about 16 to about 13, from about 15 to about 13, from about 14 to about 13, from about 18 to about 14, from about 17 to about 14, from about 16 to about 14, from about 15 to about 14, from about 18 to about 15, from about 17 to about 15, from about 16 to about 15, from about 18 to about 16, from about 17 to about 16, or from about 18 to about 17 as determined by ASTM D 1544.

Fatty Acids

The disclosed compositions can contain one or more fatty acids. By "fatty acid" is meant a carboxylic acid with at least 8 carbon atoms. "Fatty acid" is also meant to include a residue of a fatty acid. The term "residue" as used herein refers to the moiety that is the resulting product of the specified chemical species in a particular reaction scheme or subsequent formulation or chemical product, regardless of whether the moiety is actually obtained from the specified chemical species. For example, an "unsaturated fatty acid residue" refers to the moiety which results when an unsaturated fatty acid participates in a particular reaction (e.g., the residue can be an unsaturated fatty acyl group RCO— or unsaturated acyloxyl group RCOO—, where R is an unsaturated chain). In this case, the unsaturated fatty acid residue is "derived" from the unsaturated fatty acid. It is understood that this moiety can be obtained by a reaction with a species other than the specified unsaturated fatty acid, for example, by a reaction with an unsaturated fatty acid chloride, ester, or anhydride.

In some examples, the fatty acids and residues thereof that can be present in the disclosed compositions can comprise at least 8, at least 10, at least 12, at least 14, at least 16, at least 18, or at least 20 carbon atoms. In some other examples, the fatty acids or residues thereof can contain about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper and/or lower endpoint as appropriate. In still other examples, the fatty acids and residues thereof can comprise a mixture of fatty acids and residues thereof having a range of carbon atoms. For example, the fatty acids and residues thereof can comprise from about 8 to about 40, from about 10 to about 38, from about 12 to about 36, from about 14 to about 34, from about 16 to about 32, from about 18 to about 30, or from about 20 to about 28 carbon atoms.

The fatty acids and residues thereof that can be present in the disclosed compositions can be saturated, unsaturated, or a mixture of saturated and unsaturated fatty acids. By "saturated" is meant that the molecule or residue contains no carbon-carbon double or triple bounds. By "unsaturated" is meant that the molecule or residue contains at least one carbon-carbon double or triple bond. The disclosed compositions can also be processed to result in a particular mixture of fatty acids (e.g., having only saturated fatty acids, only unsaturated fatty acids, mixtures of both saturated and unsaturated fatty acids, or mixtures of fatty acids of a certain chain length or range of chain lengths).

In many examples, the disclosed compositions are derived from marine oils, plant oils, or animal oils and contain various fatty acids and residues thereof, examples of which are disclosed herein. As noted, any such oil can be used in the disclosed compositions and methods. It is also contemplated that while a particular fatty acid may not be present in the crude oil from which a specific composition is derived, such a fatty acid can be added to the composition at any time (e.g., prior, during, or after the methods disclosed herein).

Unsaturated Fatty Acids

The unsaturated fatty acids and residues thereof that can be present in the disclosed compositions contain at least one unsaturated bond (i.e., a carbon-carbon double or triple bond). In one example, the unsaturated fatty acids and residues thereof can comprise at least 2, at least 3, at least 4, at least 5, at least 6, at least 7, or at least 8 carbon-carbon double bonds triple bonds, or any combination thereof. In another example, the unsaturated fatty acids or residues thereof can comprise 1, 2, 3, 4, 5, 6, 7, or 8 unsaturated bonds, where any of the stated values can form an upper and/or lower endpoint as appropriate.

Monoene Acids and Residues

In one aspect, the unsaturated fatty acids or residues thereof can comprise one carbon-carbon double bond (i.e., a monoene acid or residue). Examples of unsaturated fatty acids and residues thereof that can be present in the disclosed compositions include, but are not limited to, those in the following Table 1.

TABLE 1

Examples of Monoenes

| Total number of carbon atoms in the fatty acid or residue chain. | Carbon number where double bond begins. ("c" denotes a cis double bond; "t" denotes a trans double bond) |
|---|---|
| 10 | 4c |
| 12 | 4c |
| 14 | 4c and 9c |
| 16 | 3t, 4c, 5t, 6c, 6t, 9c (palmitooleic), and 11c |
| 18 | 3t, 5c, 5t, 6c (petroselinic), 6t, 9c (oleic), 10c, 11c (cis-vaccenic), 11t (vaccenic), and 13c |
| 20 | 5c, 9c (gadolenic), 11c, 13c, and 15c |
| 22 | 5c, 11c (cetoleic), 13c (erucic), and 15c |
| 24 | 15c (selacholeic, nervonic) |
| 26 | 9c, and 17c (ximenic) |
| 28 | 9c, 19c (lumequic) |
| 30 | 21c |

Polyene Acids and Residues (Methylene Interrupted)

In other examples, the unsaturated fatty acids and residues thereof can comprise at least two unsaturated bonds (e.g., polyene acids or residues). In some examples, the unsaturated fatty acids and residues thereof can comprise at least one pair of methylene interrupted unsaturated bonds. By "methylene interrupted unsaturated bond" is meant that one carbon-carbon double or triple bond is separated from another carbon-carbon double or triple bond by at least one methylene group (i.e., $CH_2$). Specific examples of unsaturated fatty acids that contain at least one pair of methylene interrupted unsaturated bonds include, but are not limited to, the n-1 family derived from 9, 12, 15-16:3; n-2 family derived from 9, 12, 15-17:3, 15:3, 17:3, 17:4, 20:4; n-3 family derived from 9, 12, 15-18:3, 15:2, 15:3, 15:4, 16:3, 16:4, 18:3 (α-linolenic), 18:4, 18:5, 20:2, 20:3, 20:4, 20:5 (EPA), 21:5, 22:3, 22:5 (DPA), 22:6 (DHA), 24:3, 24:4, 24:5, 24:6, 26:5, 26:6, 28:7, 30:5; n-4 family derived from 9, 12-16:2, 16:2, 16:3, 18:2, 18:3; n-5 family derived from 9, 12-17:2, 15:2, 17:2, 17:3, 19:2, 19:4, 20:3, 20:4 21:4, 21:5; n-6 family derived from 9, 12-18:2, 15:2, 16:2,18:2 (linoleic acid), 18:3 (γ-linolenic acid); 20:2, 20:3, 20:4 (arachidonic acid), 22:2, 22:3, 22:4 (adrenic acid), 22:5, 24:2, 24:4, 25:2, 26:2, 30:4; n-7 family derived from 9-16:1, 15:2, 16:2, 17:2, 18:2, 19:2; n-8 family derived from 9-17:1, 15:2, 16:2, 17:2, 18:2, 19:2; n-9 family derived from 9-18:1, 17:2, 18:2, 20:2, 20:3, 22:3, 22:4; n-11 family 19:2, and the n-12 family 20:2.

In, the above paragraph (and throughout) the compounds are identified by referring first to the "n-x family," where x is the position in the fatty acid where the first double bond begins. The numbering scheme begins at the terminal end of the fatty acid, where, for example, the terminal $CH_3$ group is designated position 1. In this sense, the n-3 family would be an omega-3 fatty acid, as described herein. The next number identifies the total number of carbon atoms in the fatty acid.

The third number, which is after the colon, designates the total number of double bonds in the fatty acid. So, for example, in the n-1 family, 16:3, refers to a 16 carbon long fatty acid with 3 double bonds, each separated by a methylene, wherein the first double bond begins at position 1, i.e., the terminal end of the fatty acid. In another example, in the n-6 family, 18:3, refers to an 18 carbon long fatty acid with 3 methylene separated double bonds beginning at position 6, i.e., the sixth carbon from the terminal end of the fatty acid, and so forth.

Some other examples are fatty acids and residues thereof that contain at least one pair of unsaturated bonds interrupted by more than one methylene group. Suitable examples of these acids and residues thereof include, but are not limited to, those in the following Table 2.

TABLE 2

Examples of Polyene Acids and Residues with Double Bonds Interrupted by Several Methylene Units

| Total number of carbon atoms in the fatty acid or residue chain. | Carbon number where double bond begins. ("c" denotes a cis double bond; "t" denotes a trans double bond) |
|---|---|
| 18 | 5, 9 |
|  | 5, 11 |
|  | 2t, 9, 12 |
|  | 3t, 9, 12 |
|  | 5t, 9, 12 |
|  | 5, 9, 12 |
|  | 5, 11, 14 |
|  | 3t, 9, 12, 15 |
|  | 5, 9, 12, 15 |
| 20 | 5, 11 |
|  | 5, 13 |
|  | 7, 11 |
|  | 7, 13 |
|  | 5, 11, 14 |
|  | 7, 11, 14 |
|  | 5, 11, 14, 17 |
| 22 | 5, 11 |
|  | 5, 13 |
|  | 7, 13 |
|  | 7, 15 |
|  | 7, 17 |
|  | 9, 13 |
|  | 9, 15 |

Polyene Acids and Residues (Conjugated)

Still other examples of unsaturated fatty acids and residues thereof that can be present in the disclosed compositions are those that contain at least one conjugated unsaturated bond. By "conjugated unsaturated bond" is meant that at least one pair of carbon-carbon double and/or triple bonds are bonded together, without a methylene (CH$_2$) group between them (e.g., —CH═CH—CH═CH—). Specific examples of unsaturated fatty acids that contain conjugated unsaturated bonds include, but are not limited to, those in the following Table 3.

TABLE 3

Examples of Conjugated Polyene Acids and Residues

| Total number of carbon atoms in the fatty acid or residue chain. | Carbon number where double bond begins. ("c" denotes a cis double bond; "t" denotes a trans double bond) |
|---|---|
| 10 | 2t, 4t, 6c |
|  | 2c, 4t, 6t |
|  | 3t, 5t, 7c |
|  | 3c, 5t, 7t |
| 12 | 3, 5, 7, 9, 11 |

TABLE 3-continued

Examples of Conjugated Polyene Acids and Residues

| Total number of carbon atoms in the fatty acid or residue chain. | Carbon number where double bond begins. ("c" denotes a cis double bond; "t" denotes a trans double bond) |
|---|---|
| 14 | 3, 5, 7, 9, 11 |
| 18 | 10t, 12t |
|  | 8c, 10t, 12c (jacaric) |
|  | 8t, 10t, 12c (calendic) |
|  | 8t, 10t, 12t |
|  | 9t, 11t, 13c (catalpic) |
|  | 9c, 11t, 13t (α-eleostearic) |
|  | 9c, 11t, 13c (punicic) |
|  | 9t, 11t, 13t (β-eleostearic) |
|  | 9c, 11t, 13t, 15c (α-parinaric) |
|  | 9t, 11t, 13t, 15t (β-parinaric) |

Omega-3 Fatty Acids

In many examples, the disclosed compositions can comprise one or more omega-3 fatty acids or a residue thereof. An omega-3 fatty acid is an unsaturated fatty acid that contains as its terminus CH$_3$—CH$_2$—CH═CH—. Specific examples of omega-3 fatty acids that can be present in the disclosed compositions include, but are not limited to, linolenic acid (18:3ω3), octadecatetraenoic acid (18:4ω3), eicosapentaenoic acid (20:5%3) (EPA), docosahexaenoic acid (22:6ω3) (DHA), docosapentaenoic acid (22:6ω3) (DPA), including residues, derivatives, and mixtures thereof.

In still other examples, the unsaturated fatty acids or residues thereof can be derived from a compound comprising the following formula:

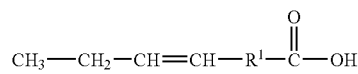

wherein R$^1$ is a C$_3$-C$_{40}$ alkyl or alkenyl group comprising at least one double bond. The term "alkane" or "alkyl" as used herein is a saturated hydrocarbon group. The term "alkene" or "alkenyl" as used herein is a hydrocarbon group containing at least one carbon-carbon double bond. Asymmetric structures such as (AB)C═C(CD) are intended to include both the E and Z isomers (cis and trans). This may be presumed in structural formulae herein wherein an asymmetric alkene is present, or it may be explicitly indicated by the bond symbol C═C. In a further example, R$^1$ can be a C$_5$-C$_{38}$, C$_6$-C$_{36}$, C$_8$-C$_{34}$, C$_{10}$-C$_{32}$, Cl$_{12}$-C$_{30}$, C$_{14}$-C$_{28}$, C$_{16}$-C$_{26}$, or C$_{18}$-C$_{24}$ alkenyl group. In yet another example, the alkenyl group of R$^1$ can have from 2 to 6, from 3 to 6, from 4 to 6, or from 5 to 6 double bonds. Still further, the alkenyl group of R$^1$ can have from 1, 2, 3, 4, 5, or 6 double bonds, where any of the stated values can form an upper or lower endpoint when appropriate.

Exemplary Unsaturated Fatty Acids

Some specific examples of unsaturated fatty acids and residues derived therefrom that can be present in the disclosed compositions include, but are not limited to, linoleic acid, linolenic acid, γ-linolenic acid, arachidonic acid, mead acid, stearidonic acid, α-eleostearic acid, eleostearic acid, pinolenic acid, docosadienic acid, docosatetraenoic acid, docosapentaenoic acid, docosahexaenoic acid, octadecadienoic acid, octadecatrienoic acid, eicosatetraenoic acid, eicosapentaenoic, or any combination thereof. In one aspect, the unsaturated fatty acid residue can be derived from eicosapentaenoic acid 20:5ω3 (EPA), docosahexaenoic acid 22:6ω3 (DHA), docosapentaenoic acid 22:5ω3 (DPA), and any combination thereof.

Amounts of DHA/EPA

As noted many of the disclosed compositions can contain the omega-3 fatty acids EPA and DHA or a residue thereof. Each of these unsaturated fatty acids or residues can be present in the disclosed compositions in an amount of from about 0 to about 700 milligrams per gram of the composition. In other examples, DHA and/or EPA can each be present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700 milligrams per grain of the composition, where any of the stated values can form an upper and/or lower endpoint as appropriate.

In still other examples, DHA and/or EPA can each be present in the disclosed compositions in an amount from about 50 to about 700, from about 100 to about 700, from about 150 to about 700, from about 200 to about 700, from about 250 to about 700, from about 300 to about 700, from about 350 to about 700, from about 400 to about 700, from about 450 to about 700, from about 500 to about 700, from about 550 to about 700, from about 600 to about 700, from about 650 to about 700, from about 0 to about 650, from about 50 to about 650, from about 100 to about 650, from about 10 to about 650, from about 200 to about 650, from about 250 to about 650, from about 300 to about 650, from about 350 to about 650, from about 400 to about 650, from about 450 to about 650, from about 500 to about 650, from about 550 to about 650, from about 600 to about 650, from about 0 to about 600, from about 50 to about 600, from about 100 to about 600, from about 150 to about 600, from about 200 to about 600, from about 250 to about 600, from about 300 to about 600, from about 350 to about 600, from about 400 to about 600, from about 450 to about 600, from about 500 to about 600, from about 550 to about 600, from about 0 to about 550, from about 50 to about 550, from about 500 to about 550, from about 150 to about 550, from about 200 to about 550, from about 250 to about 550, from about 300 to about 550, from about 350 to about 550, from about 400 to about 550, from about 450 to about 550, from about 500 to about 550, from about 0 to about 500, from about 50 to about 500, from about 100 to about 500, from about 150 to about 500, from about 200 to about 500, from about 250 to about 500, from about 300 to about 500, from about 350 to about 500, from about 400 to about 500, from about 450 to about 500, from about 0 to about 450, from about 50 to about 450, from about 100 to about 450, from about 150 to about 450, from about 200 to about 450, from about 250 to about 450, from about 300 to about 450, from about 350 to about 450, from about 400 to about 450, from about 0 to about 400, from about 350 to about 400, from about 100 to about 400, from about 150 to about 400, from about 200 to about 400, from about 250 to about 400, from about 300 to about 400, from about 350 to about 400, from about 0 to about 350, from about 50 to about 350, from about 100 to about 350, from about 150 to about 350, from about 200 to about 350, from about 250 to about 350, from about 300 to about 350, from about 0 to about 300, from about 50 to about 300, from about 100 to about 300, from about 150 to about 300, from about 200 to about 300, from about 250 to about 300, from about 0 to about 250, from about 50 to about 250, from about 100 to about 250, from about 150 to about 250, from about 200 to about 250, from about 0 to about 200, from about 50 to about 200, from about 100 to about 200, from about 150 to about 200, from about 0 to about 150, from about 50 to about 150, from about 100 to about 150, from about 0 to about 100, from about 50 to about 100, from about 0 to about 50 milligrams per gram of composition.

The amount of EPA and DHA that can be present in the disclosed compositions can also be described in terms of weight % (wt. %). For example, the disclosed compositions can comprise from about 0 to about 70 wt. % EPA and/or DHA, based on the total weight of the composition. In other examples, the disclosed compositions can comprise about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 wt. % based on the total weight of the composition, where any of the stated values can form an upper and/or lower endpoint as appropriate.

In still further examples, the amount of EPA and/or DHA that can be present in the disclosed composition can be from about 5 to about 70, from about 10 to about 70, from about 15 to about 70, from about 20 to about 70, from about 25 to about 70, from about 30 to about 70, from about 35 to about 70, from about 40 to about 70, from about 45 to about 70, from about 50 to about 70, from about 55 to about 70, from about 60 to about 70, from about 65 to about 70, from about 0 to about 65, from about 5 to about 65, from about 10 to about 65, from about 15 to about 65, from about 20 to about 65, from about 25 to about 65, from about 30 to about 65, from about 35 to about 65, from about 40 to about 65, from about 45 to about 65, from about 50 to about 65, from about 55 to about 65, from about 60 to about 65, from about 0 to about 60, from about 5 to about 60, from about 10 to about 60, from about 15 to about 60, from about 20 to about 60, from about 25 to about 60, from about 30 to about 60, from about 35 to about 60, from about 40 to about 60, from about 45 to about 60, from about 50 to about 60, from about 55 to about 60, from about 0 to about 55, from about 5 to about 55, from about 10 to about 55, from about 15 to about 55, from about 20 to about 55, from about 25 to about 55, from about 30 to about 55, from about 35 to about 55, from about 40 to about 55, from about 45 to about 55, from about 50 to about 55, from about 0 to about 50, from about 5 to about 50, from about 10 to about 50, from about 15 to about 50, from about 20 to about 50, from about 25 to about 50, from about 30 to about 50, from about 35 to about 50, from about 40 to about 50, from about 45 to about 50, from about 0 to about 45, from about 5 to about 45, from about 10 to about 45, from about 15 to about 45, from about 20 to about 45, from about 25 to about 45, from about 30 to about 45, from about 35 to about 45, from about 40 to about 45, from about 0 to about 40, from about 5 to about 40, from about 10 to about 40, from about 15 to about 40, from about 20 to about 40, from about 25 to about 40, from about 30 to about 40, from about 35 to about 40, from about 0 to about 35, from about 5 to about 35, from about 10 to about 35, from about 15 to about 35, from about 20 to about 35, from about 25 to about 35, from about 30 to about 35, from about 0 to about 30, from about 5 to about 30, from about 10 to about 30, from about 15 to about 30, from about 20 to about 30, from about 25 to about 30, from about 0 to about 25, from about 5 to about 25, from about 10 to about 25, from about 15 to about 25, from about 20 to about 25, from about 0 to about 20, from about 5 to about 20, from about 10 to about 20, from about 15 to about 20, from about 0 to about 15, from about 5 to about 15, from about 10 to about 15, from about 0 to about 10, from about 5 to about 10, from about 0 to about 5 wt. % based on the total weight of the composition. In some other specific examples, the amount of EPA and/or DHA that can be present in the disclosed compositions can be about 0.3, 5, 12, 18, 25, or 60 wt. % based on the total weight of the composition, where any of the stated values can form an upper and/or lower endpoint when appropriate.

The amount of EPA and DHA present in the disclosed compositions can also be described in terms of the wt. % ratio of EPA to DHA. For example, the wt. % ratio of EPA to DHA in the disclosed compositions can be about 18:12 (i.e., about 18 wt. % EPA to about 12 wt. % DHA, based on the total weight of the composition). Other wt. % ratios of EPA to DHA that can be present in the disclosed compositions include, but are not limited to, about 5:25, about 60:0.3, and about 0.8:60. Further wt. % ratios of EPA to DHA for the disclosed compositions can be about 0:70, 5:70, 10:70, 15:70, 20:70, 25:70, 30:70, 70:30, 70:25, 70:20, 70:15, 70:10, 70:5, 70:0, 0:65, 5:65, 10:65, 15:65, 20:65, 25:65, 30:65, 35:65, 65:35, 65:30, 65:25, 65:20, 65:15, 65:10, 65:5, 65:0, 0:60, 5:60, 10:60, 15:60, 20:60, 25:60, 30:60, 35:60, 40:60, 60:40, 60:35, 60:30, 60:25, 60:20, 60:15, 60:10, 60:5, 60:0, 0:55, 5:55, 10:55, 15:55, 20:55, 25:55, 30:55, 35:55, 40:55, 45:55, 55:45, 55:40, 55:35, 55:30, 55:25, 55:20, 55:15, 55:10, 55:5, 55:0, 0:50, 5:50, 10:50, 15:50, 20:50, 25:50, 30:50, 35:50, 40:50, 45:50, 50:50, 50:45, 50:40, 50:35, 50:30, 50:25, 50:20, 50:15, 50:10, 50:5, 50:0, 0:45, 5:45, 10:45, 15:45, 20:45, 25:45, 30:45, 35:45, 40:45, 45:45, 45:40, 45:35, 45:30, 45:25, 45:20, 45:15, 45:10, 45:5, 45:0, 0:40, 5:40, 10:40, 15:40, 20:40, 25:40, 30:40, 35:40, 40:40, 40:35, 40:30, 40:25, 40:20, 40:15, 40:10, 40:5, 40:0, 0:35, 5:35, 10:35, 15:35, 20:35, 25:35, 30:35, 35:35, 35:30, 35:25, 35:20, 35:15, 35:10, 35:5, 35:0, 0:30, 5:30, 10:30, 15:30, 20:30, 25:30, 30:30, 30:25, 30:20, 30:15, 30:10, 30:5, 30:0, 0:25, 5:25, 10:25, 15:25, 20:25, 25:25, 25:20, 25:15, 25:10, 25:5, 25:0, 0:20, 5:20, 10:20, 15:20, 20:20, 20:15, 20:10, 20:5, 20:0, 0:15, 5:15, 10:15, 15:15, 15:10, 15:5, 15:0, 0:10, 5:10, 10:10, 10:5, 10:0, 0:5, 5:5, or 5:0.

Additional Fatty Acids

Examples of additional fatty acids and residues thereof that can be present in the disclosed compositions include, but are not limited to, the saturated fatty acids capric acid (C10), lauric acid (C12), myristic acid (C14), palmitic acid (C16), margaric acid (C17), stearic acid (C18), arachidic acid (C20), behenic acid (C22), lignoceric acid (C24), cerotic acid (C26), montanic acid (C28), and melissic acid (C30), including branched and substituted derivatives thereof.

Additional examples of unsaturated fatty acids that can be present in the disclosed compositions include, but are not limited to, allenic and acetylenic acids, such as, C14: 2, 4, 5; C18: 5, 6 (laballenic); 5, 6, 16 (lamenallenic); C18: 6a (tarinic); 9a; 9a, 11t (ximenynic); 9a, 11a; 9a, 11a, 13c (bolekic); 9a, 11a, 13a, 15e, 8a, 10t (pyrulic) 9c, 12a (crepenynic), 9c, 12a, 14c (dehydrocrepenynic acid); 6a, 9c, 12c; 6a, 9c, 12c, 15c, 8a, 11c, 14c and corresponding Δ17e derivatives, 8-OH derivatives, and Δ17e, 8-OH derivatives. Branched-chain acids, particularly iso-acids and anteiso acids, polymethyl branched acids, phytol based acids (e.g., phytanic, pristanic), furanoid acids are also suitable fatty acids, including the residues derived therefrom, that can be present in the disclosed compositions. Still further fatty acids and residues thereof include, but are not limited to, cyclic acids, such as cyclopropane fatty acids, cyclopropene acids (e.g., lactobacillic), sterulic, malvalic, sterculynic, 2-hydroxysterculic, aleprolic, alepramic, aleprestic, aleprylic alepric, hydnocarpic, chaulmoogric hormelic, manaoic, gorlic, oncobic, cyclopentenyl acids, and cyclohexylalkanoic acids. Hydroxy acids, particularly butolic, ricinoleic, isoricinoleic, densipolic, lesquerolic, and auriolic are also suitable fatty acids that can be present in the disclosed compositions. Epoxy acids, particularly epoxidated C18:1 and C18:2, and furanoid acids are further examples of fatty acids that can be present in the disclosed compositions.

Trans Fatty Acids

In still other examples, the disclosed compositions can also contain various amounts of trans-fatty acids. Trans-fatty acids are unsaturated fatty acids where at least one double bond is a trans-double bond. The amount of trans-fatty acids in the disclosed compositions can be less than or equal to about 5 wt. % based on the total weight of the composition. In other examples, the amount of trans-fatty acids can be less than or equal to about 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 wt. % based on the total weight of the composition, where any of the stated values can form an upper and/or lower endpoint as appropriate. The amount of trans fatty acids can also be about 0 wt. %.

In further examples, the disclosed compositions can contain from about 5.0 to about 0.0, from about 4.5 to about 0.0, from about 4.0 to about 0.0, from about 3.5 to about 0.0, from about 3.0 to about 0.0, from about 2.5 to about 0.0, from about 2.0 to about 0.0, from about 1.5 to about 0.0, from about 1.0 to about 0.0, from about 0.5 to about 0.0, from about 5.0 to about 0.5, from about 4.5 to about 0.5, from about 4.0 to about 0.5, from about 3.5 to about 0.5, from about 3.0 to about 0.5, from about 2.5 to about 0.5, from about 2.0 to about 0.5, from about 1.5 to about 0.5, from about 1.0 to about 0.5, from about 5.0 to about 1.0, from about 4.5 to about 1.0, from about 4.0 to about 1.0, from about 3.5 to about 1.0, from about 3.0 to about 1.0, from about 2.5 to about 1.0, from about 2.0 to about 1.0, from about 1.5 to about 1.0, from about 5.0 to about 2.0, from about 4.5 to about 2.0, from about 4.0 to about 2.0, from about 3.5 to about 2.0, from about 3.0 to about 2.0, from about 2.5 to about 2.0, from about 5.0 to about 2.5, from about 4.5 to about 2.5, from about 4.0 to about 2.5, from about 3.5 to about 2.5, from about 3.0 to about 2.5, from about 5.0 to about 3.0, from about 4.5 to about 3.0, from about 4.0 to about 3.0, from about 3.5 to about 3.0, from about 5.0 to about 3.5, from about 4.5 to about 3.5, from about 4.0 to about 3.5, from about 5.0 to about 4.0, from about 4.5 to about 4.0, from about 5.0 to about 4.5, wt. % of trans-fatty acids, based on the total weight of the composition.

Oxidized Fatty Acids

The disclosed compositions can also contain low levels of oxidized fatty acids and/or aldehydes. For example, many oils containing unsaturated fatty acids can oxidize and break down, resulting in the production of volatile aldehydes like hexanal and a non-volatile portion of the oxidized fatty acid, which remains a part of the composition. The compositions disclosed herein can have reduced levels of such oxidized fatty acids and/or aldehydes, as compared to other marine oils.

The amount of the aldehydes and oxidized fatty acids in an oil can be measured by reacting the oil with p-Anisidine and determining the p-Anisidine value. The p-Anisidine value is defined as 100 times the absorbance (at 350 nm) of a solution resulting from reaction of 1 gram of oil in 100 mL of solvent. p-Anisidine values can be determined by well known methods such as the method described in ISO method number 6885:1998, which is available from the International Organization for Standardization; this method is incorporated by reference herein in its entirety.

Typical p-Anisidine values for crude marine oil can be about 20. The compositions disclosed herein, however, can have p-Anisidine values of less than or equal to about 25. In other examples, the disclosed compositions can have p-Anisidine values of less than or equal to about 25, 24, 23, 22, 21, 20, 19, 18, 17, 16, 15, 14, 13, 12, 11, 10, 9, 8, 7, 6, 5, 4, 3, 2, or 1 as determined by ISO 6885:1998, where any of the stated values can form an upper and/or lower endpoint as appropriate.

In other examples of the disclosed compositions, the p-Anisidine value can be from about 25 to about 1, from about 24 to about 1, from about 23 to about 1, from about 22 to about 1, from about 21 to about 1, from about 20 to about 1, from about 19 to about 1, from about 18 to about 1, from about 17 to about 1, from about 16 to about 1, from about 15 to about 1, from about 14 to about 1, from about 13 to about 1, from about 12 to about 1, from about 11 to about 1, from about 10 to about 1, from about 9 to about 1, from about 8 to about 1, from about 7 to about 1, from about 6 to about 1, from about 5 to about 1, from about 4 to about 1, from about 3 to about 1, from about 2 to about 1, from about 25 to about 2, from about 24 to about 2, from about 23 to about 2, from about 22 to about 2, from about 21 to about 2, from about 20 to about 2, from about 19 to about 2, from about 18 to about 2, from about 17 to about 2, from about 16 to about 2, from about 15 to about 2, from about 14 to about 2, from about 13 to about 2, from about 12 to about 2, from about 11 to about 2, from about 10 to about 2, from about 9 to about 2, from about 8 to about 2, from about 7 to about 2, from about 6 to about 2, from about 5 to about 2, from about 4 to about 2, from about 3 to about 2, from about 25 to about 3, from about 24 to about 3, from about 23 to about 3, from about 22 to about 3, from about 21 to about 3, from about 20 to about 3, from about 19 to about 3, from about 18 to about 3, from about 17 to about 3, from about 16 to about 3, from about 15 to about 3, from about 14 to about 3, from about 13 to about 3, from about 12 to about 3, from about 11 to about 3, from about 10 to about 3, from about 9 to about 3, from about 8 to about 3, from about 7 to about 3, from about 6 to about 3, from about 5 to about 3, from about 4 to about 3, from about 25 to about 4, from about 24 to about 4, from about 23 to about 4, from about 22 to about 4, from about 21 to about 4, from about 20 to about 4, from about 19 to about 4, from about 18 to about 4, from about 17 to about 4, from about 16 to about 4, from about 15 to about 4, from about 14 to about 4, from about 13 to about 4, from about 12 to about 4, from about 11 to about 4, from about 10 to about 4, from about 9 to about 4, from about 8 to about 4, from about 7 to about 4, from about 6 to about 4, from about 5 to about 4, from about 25 to about 5, from about 24 to about 5, from about 23 to about 5, from about 22 to about 5, from about 21 to about 5, from about 20 to about 5, from about 19 to about 5, from about 18 to about 5, from about 17 to about 5, from about 16 to about 5, from about 15 to about 5, from about 14 to about 5, from about 13 to about 5, from about 12 to about 5, from about 11 to about 5, from about 10 to about 5, from about 9 to about 5, from about 8 to about 5, from about 7 to about 5, from about 6 to about 5, from about 25 to about 6, from about 24 to about 6, from about 23 to about 6, from about 22 to about 6, from about 21 to about 6, from about 20 to about 6, from about 19 to about 6, from about 18 to about 6, from about 17 to about 6, from about 16 to about 6, from about 15 to about 6, from about 14 to about 6, from about 13 to about 6, from about 12 to about 6, from about 11 to about 6, from about 10 to about 6, from about 9 to about 6, from about 8 to about 6, from about 7 to about 6, from about 25 to about 7, from about 24 to about 7, from about 23 to about 7, from about 22 to about 7, from about 21 to about 7, from about 20 to about 7, from about 19 to about 7, from about 18 to about 7, from about 17 to about 7, from about 16 to about 7, from about 15 to about 7, from about 14 to about 7, from about 13 to about 7, from about 12 to about 7, from about 11 to about 7, from about 10 to about 7, from about 9 to about 7, from about 8 to about 7, from about 25 to about 8, from about 24 to about 8, from about 23 to about 8, from about 22 to about 8, from about 21 to about 8, from about 20 to about 8, from about 19 to about 8, from about 18 to about 8, from about 17 to about 8, from about 16 to about 8, from about 15 to about 8, from about 14 to about 8, from about 13 to about 8, from about 12 to about 8, from about 11 to about 8, from about 10 to about 8, from about 9 to about 8, from about 25 to about 9, from about 24 to about 9, from about 23 to about 9, from about 22 to about 9, from about 21 to about 9, from about 20 to about 9, from about 19 to about 9, from about 18 to about 9, from about 17 to about 9, from about 16 to about 9, from about 15 to about 9, from about 14 to about 9, from about 13 to about 9, from about 12 to about 9, from about 11 to about 9, from about 10 to about 9, from about 25 to about 10, from about 24 to about 10, from about 23 to about 10, from about 22 to about 10, from about 21 to about 10, from about 20 to about 10, from about 19 to about 10, from about 18 to about 10, from about 17 to about 10, from about 16 to about 10, from about 15 to about 10, from about 14 to about 10, from about 13 to about 10, from about 12 to about 10, from about 11 to about 10, from about 25 to about 11, from about 24 to about 11, from about 23 to about 11, from about 22 to about 11, from about 21 to about 11, from about 20 to about 11, from about 19 to about 11, from about 18 to about 11, from about 17 to about 11, from about 16 to about 11, from about 15 to about 11, from about 14 to about 11, from about 13 to about 11, from about 12 to about 11, from about 25 to about 12, from about 24 to about 12, from about 23 to about 12, from about 22 to about 12, from about 21 to about 12, from about 20 to about 12, from about 19 to about 12, from about 18 to about 12, from about 17 to about 12, from about 16 to about 12, from about 15 to about 12, from about 14 to about 12, from about 13 to about 12, from about 25 to about 13, from about 24 to about 13, from about 23 to about 13, from about 22 to about 13, from about 21 to about 13, from about 20 to about 13, from about 19 to about 13, from about 18 to about 13, from about 17 to about 13, from about 16 to about 13, from about 15 to about 13, from about 14 to about 13, from about 25 to about 14, from about 24 to about 14, from about 23 to about 14, from about 22 to about 14, from about 21 to about 14, from about 20 to about 14, from about 19 to about 14, from about 18 to about 14, from about 17 to about 14, from about 16 to about 14, from about 15 to about 14, from about 25 to about 15, from about 24 to about 15, from about 23 to about 15, from about 22 to about 15, from about 21 to about 15, from about 20 to about 15, from about 19 to about 15, from about 18 to about 15, from about 17 to about 15, from about 16 to about 15, from about 25 to about 16, from about 24 to about 16, from about 23 to about 16, from about 22 to about 16, from about 21 to about 16, from about 20 to about 16, from about 19 to about 16, from about 18 to about 16, from about 17 to about 16, from about 25 to about 17, from about 24 to about 17, from about 23 to about 17, from about 22 to about 17, from about 21 to about 17, from about 20 to about 17, from about 19 to about 17, from about 18 to about 17, from about 25 to about 18, from about 24 to about 18, from about 23 to about 18, from about 22 to about 18, from about 21 to about 18, from about 20 to about 18, from about 19 to about 18, from about 25 to about 19, from about 24 to about 19, from about 23 to about 19, from about 22 to about 19, from about 21 to about 19, from about 20 to about 19, from about 25 to about 20, from about 24 to about 20, from about 23 to about 20, from about 22 to about 20, from about 21 to about 20, from about 25 to about 21, from about 24 to about 21, from about 23 to about 21, from about 22 to about 21, from about 25 to about 22, from about 24 to about 22, from about 23 to about 22, from about 25 to about 23, from about 24 to about 23, or from about 25 to about 24 as determined by ISO 6885:1998.

Levels of Mono-, Di-, and Tri-glycerides

The disclosed compositions can also comprise high levels of triglycerides. Triglycerides are esters of fatty acids, such as those disclosed herein, and a tri-functional alcohol, i.e., 1,2,3-propantriol, which is also known as glycerol. In many examples, the disclosed compositions can comprise greater than or equal to about 97 wt. % triglycerides based on the total weight of the composition. In other examples, the disclosed compositions can comprise about 97.5, 98.0, 98.5, 99.0, 99.5, 99.7, 99.9, or 100 wt. % triglycerides based on the total weight of the composition, where any of the stated values can form an upper and/or lower endpoint when appropriate. In still other examples, the disclosed compositions can comprise from about 97.0 to about 100.0, from about 97.5 to about 100.0, from about 98.0 to about 100.0, from about 98.5 to about 100.0, from about 99.0 to about 100.0, from about 99.5 to about 100.0, from about 99.7 to about 100.0, from about 99.9 to about 100.0, from about 97.0 to about 99.9, from about 97.5 to about 99.9, from about 98.0 to about 99.9, from about 98.5 to about 99.9, from about 99.0 to about 99.9, from about 99.5 to about 99.9, from about 99.7 to about 99.9, from about 97.0 to about 99.7, from about 97.5 to about 99.7; from about 98.0 to about 99.7, from about 98.5 to about 99.7, from about 99.0 to about 99.7, from about 99.5 to about 99.7, from about 97.0 to about 99.5, from about 97.5 to about 99.5, from about 98.0 to about 99.5, from, about 98.5 to about 99.5, from about 99.0 to about 99.5, from about 97.0 to about 99.0, from about 97.5 to about 99.0, from about 98.0 to about 99.0, from about 98.5 to about 99.0, from about 97.0 to about 98.5, from about 97.5 to about 98.5, from about 98.0 to about 98.5, from about 97.0 to about 98.0, from about 97.5 to about 98.0, from about 97.0 to about 97.5 wt. % triglycerides based on the total weight of the composition.

Also, the disclosed compositions can comprise less than or equal to about 2 wt. % di- and/or mono-glycerides based on the total weight of the composition. For example, the disclosed compositions can comprise less than or equal to about 1.5, 1.0, 0.5, or 0.0 wt. % di- and/or mono-glycerides based on the total weight of the composition, where any of the stated values can form an upper and/or lower endpoint as appropriate. In a particular example, the disclosed compositions can comprise 0.0 wt. % monoglycerides.

Methods of Making

The disclosed compositions can be prepared by methods disclosed herein. That is, the disclosed methods can be used to reduce and/or remove compounds (e.g. sterols) from oils (e.g., marine oils, plant oils, and animal oils), producing the disclosed compositions. In one aspect, the disclosed methods comprise contacting an oil with an adsorbent to provide a mixture, heating the mixture to from about 100 to about 210° C., and removing the adsorbent from the mixture, to provide the disclosed composition. In a specific example, disclosed herein is a method for preparing a low-cholesterol composition by contacting an oil with an adsorbent to provide a mixture, heating the mixture to from about 100 to about 210° C., and removing the adsorbent from the mixture. These disclosed methods can be used to provide a low-cholesterol composition wherein the composition comprises, for example, less than about 2.0 milligrams of cholesterol per gram of the composition.

As noted, the resulting composition can comprise reduced levels of compounds such as sterols, as is described above. Further, the resulting compositions can comprise levels of EPA/DHA, Gardner color, p-Anisidine values, trans-fatty acid levels, and/or mono-, di-, and tri-glyceride levels as described above.

Adsorbent

In the disclosed methods, the adsorbent can be silica, clay, carbon, or a mixture thereof. Suitable examples of silica can be TRYSIL™, which is available from Grace Davison (Columbia Md.). Suitable examples of clay can be Grade F-160 activated clay, which is available from manufactured by Englehardt Corporation (Jackson, Miss.).

In some examples of the disclosed methods, the adsorbent can be a combination of silica and clay. Suitable combinations can comprise silica and clay in a weight ratio of about 1:1. In other examples, the adsorbent can comprise silica and clay in a weight ratio of about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1.

In the disclosed methods, the amount of adsorbent used can be from less than or equal to about 20 wt. %, based on the weight of the oil. For example, the adsorbent can used in an amount of about 20, 19, 18, 17, 16, 15, 14, 13, 12, 11, 10, 9, 8, 7, 6, 5, 4, 3, 2, or 1 wt. %, based on the weight of the oil, where any of the stated values can form an upper and/or lower endpoint as appropriate. In other examples, the adsorbent can be used in an amount of from about 20 to about 2, from about 18 to about 2, from about 16 to about 2, from about 14 to about 2, from about 12 to about 2, from about 10 to about 2, from about 8 to about 2, from about 6 to about 2, from about 4 to about 2, from about 20 to about 4, from about 18 to about 4, from about 16 to about 4, from about 14 to about 4, from about 12 to about 4, from about 10 to about 4, from about 8 to about 4, from about 6 to about 4, from about 20 to about 6, from about 18 to about 6, from about 16 to about 6, from about 14 to about 6, from about 12 to about 6, from about 10 to about 6, from about 8 to about 6, from about 20 to about 8, from about 18 to about 8, from about 16 to about 8, from about 14 to about 8, from about 12 to about 8, from about 10 to about 8, from about 20 to about 10, from about 18 to about 10, from about 16 to about 10, from about 14 to about 10, from about 12 to about 10, from about 20 to about 12, from about 18 to about 12, from about 16 to about 12, from about 14 to about 12, from about 20 to about 14, from about 18 to about 14, from about 16 to about 14, from about 20 to about 16, from about 18 to about 16, or from about 20 to about 18 wt. %, based on the weight of the oil.

Also, the ratio of adsorbent to oil that can be used can be about 20:100, 19:100, 18:100, 17:100, 16:100, 15:100, 14:100, 13:100, 12:100, 11:100, 1:10, 9:100, 8:100, 7:100, 6:100, 5:100, 4:100, 3:100, 2:100, or 1:100. When the adsorbent is a combination of silica and clay, the individual ratios of silica and clay to oil that can be used can be about 1:10, 9:100, 8:100, 7:100, 6:100, 5:100, 4:100, 3:100, 2:100, or 1:100. Also, when the adsorbent is a combination of silica and clay, each can be used in an amount of about 20, 19, 18, 17, 16, 15, 14, 13, 12, 11, 10, 9, 8, 7, 6, 5, 4, 3, 2, or 1 wt. %, based on the weight of the oil, where any of the stated values can form an upper and/or lower endpoint as appropriate. In several examples, from about 3 to about 7 wt. % (e.g. or from about 5 to about 7 wt. %) of the adsorbent is contacted to the oil.

Mixing

The adsorbent and oil can be mixed by any methods known in the art. "Mixing" is not meant to imply a particular outcome of mixing, such as the dissolution of any components to a particular level or the formation of a particular composition, such as homogeneous mixture, although such mixtures can be produced and some components can be dissolved by mixing. It can be desired that the mixing be vigorous. Mixing can be performed manually or by a mechanical mixing device such as, but not limited to, a static mixer, a magnetic stirrer, a shaker, spinner, or rotating device. Mixing can also be performed by forcing or bubbling a gas through the mixture or by sonication.

Mixing the oil and adsorbent can be performed for at least 1 minute. Mixing can also be performed for at least 1, 5, 15, 20, 25, 30, 35, 40, 45, 50, 55, 60, 65, 70, 75, 80, 85, 90, 95, or 100 minutes, where any of the stated values can form an upper and/or lower endpoint as appropriate. Also, the mixture can be mixed before, during, or after the heating step.

Temperature

Heating the mixture of adsorbent and oil can be performed at various temperatures, but, typically, the method can take place at an elevated temperature. The precise elevated temperature can depend on the particular oil and amount thereof being used, the particular adsorbent and the amount thereof being used, the ratio of oil to the adsorbent, the particular pressure, preference, and the like. Suitable temperatures at which the disclosed methods can be performed include, but are not limited to, from about 100 to about 210° C., from about 110 to about 200° C., from about 120 to about 190° C., from about 130 to about 180° C., from about 140 to about 170° C., or from about 150 to about 160° C. In other examples, the mixture can be heated to about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, or 210° C., where any of the stated values can form an upper and/or lower endpoint as appropriate.

In yet other examples, the mixture can be heated to from about 100 to about 210, from about 110 to about 210, from about 120 to about 210, from about 130 to about 210, from about 140 to about 210, from about 150 to about 210, from about 160 to about 210, from about 170 to about 210, from about 180 to about 210, from about 190 to about 210, from about 200 to about 210, from about 100 to about 200, from about 110 to about 200, from about 120 to about 200, from about 130 to about 200, from about 140 to about 200, from about 150 to about 200, from about 160 to about 200, from about 170 to about 200, from about 180 to about 200, from about 190 to about 200, from about 100 to about 190, from about 110 to about 190, from about 130 to about 190, from about 140 to about 190, from about 150 to about 190, from about 160 to about 190, from about 170 to about 190, from about 180 to about 190, from about 100 to about 180, from about 110 to about 180, from about 120 to about 180, from about 140 to about 180, from about 150 to about 180, from about 160 to about 180, from about 170 to about 180, from about 100 to about 170, from about 110 to about 170, from about 120 to about 170, from about 130 to about 170, from about 150 to about 170, from about 160 to about 170, from about 100 to about 160, from about 110 to about 160, from about 120 to about 160, from about 130 to about 160, from about 140 to about 160, from about 100 to about 150, from about 110 to about 150, from about 120 to about 150, from about 130 to about 150, from about 140 to about 150, from about 100 to about 140, from about 110 to about 140, from about 120 to about 140, from about 130 to about 140, from about 100 to about 130, from about 110 to about 130, from about 120 to about 130, from about 100 to about 120, from about 110 to about 120, or from about 100 to about 110° C. In some specific examples, the mixture can be heated to from about 140 to about 180° C. or, more specifically, from about 180 to about 190° C. or from about 150 to about 170° C.

It is also contemplated that the oil is heated prior to contacting with the adsorbent. Such a pre-heating step can be performed at any of temperatures and temperature ranges described herein.

Heating the mixture and/or pre-heating the oil can take place over a period of time, for example for at least 1, 10, 20, 30, 40, 50, or 60 minutes. In some examples, the heating step is performed for from about 10 to about 20, from about 20 to about 30, from about 10 to about 30, or from about 30 to about 60 minutes. Further, after heating, the mixture can be allowed to cool from about 30 to about 60 minutes.

Pressure

In the disclosed methods, the heating step can be conducted under reduced pressure. A suitable pressure is less than or equal to about 1 Torr or less than or equal to about 0.1 Torr. In other examples, the heating step can be conducted at a pressure of less than or equal to about 1, 0.9, 0.8, 0.7, 0.6, 0.5, 0.4, 0.3, 0.2, 0.1, 0.09, 0.08, 0.07, 0.06, 0.05, 0.04, 0.03, 0.02, or 0.01, where any of the stated values can form an upper and/or lower endpoint when appropriate.

Separation

After the mixture is heated, the adsorbent can be removed from the mixture. Removing the adsorbent can be performed by any methods known in the art. For example, the adsorbent can be removed by filtration, centrifugation, or other like methods. The compositions that result from heating the oil with the adsorbent, and also from removing the adsorbent, can comprise a reduced content of cholesterol (e.g., less than or equal to about 6 mg of cholesterol per gram of oil), a p-Anisidine value of less than or equal to about 25, a Gardner color of less than or equal to about 18, from about 0 to about 700 milligrams of DHA and/or EPA per gram of the composition (or a EPA:DHA wt. % ratio of from 0:70 to 70:0), less than or equal to about 5 wt. % trans-fatty acids, and/or greater than or equal to about 97 wt. % triglycerides. The composition obtained includes cholesterol-free product. The process also can be used as bleaching process for a dual purpose, i.e. to reduce cholesterol and color from oil.

Supplements

Also, disclosed herein are nutritional supplements comprising the compositions disclosed herein. A nutritional supplement is any compound or composition that can be administered to or taken by a subject to provide, supply, or increase a nutrient(s) (e.g., vitamin, mineral, essential trace element, amino acid, peptide, nucleic acid, oligonucleotide, lipid, cholesterol, steroid, carbohydrate, and the like). In one aspect, disclosed herein are nutritional supplements comprising any of the compounds disclosed herein. For example, a nutritional supplement can comprise a composition comprising a marine oil, wherein the composition has less than or equal to about 6 mg of cholesterol per gram of oil, a p-Anisidine value of less than or equal to 25, a Gardner color of less than or equal to 18, from about 0 to about 700 milligrams of DHA and/or EPA per gram of the composition (or a EPA: DHA wt. % ratio of from 0:70 to 70:0), less or equal to about 5 wt. % trans-fatty acids, and/or greater than or equal to about 97 wt. % triglycerides.

The nutritional supplement can comprise any amount of the compositions disclosed herein, but will typically contain an amount determined to supply a subject with a desired dose of an oil or particular fatty acid (e.g., EPA and/or DHA). The exact amount of compound required in the nutritional supplement will vary from subject to subject, depending on the species, age, weight and general condition of the subject, the severity of any dietary deficiency being treated, the particular mode of administration, and the like. Thus, it is not possible to specify an exact amount for every nutritional supplement. However, an appropriate amount can be determined by one of ordinary skill in the art using only routine experimentation given the teachings herein.

The nutritional supplement can also comprise other nutrient(s) such as vitamins other trace elements, minerals, and the like. Further, the nutritional supplement can comprise other components such as preservatives, antimicrobials, anti-oxidants, chelating agents, thickeners, flavorings, diluents, emulsifiers, dispersing aids, or binders.

The nutritional supplements are generally taken orally and can be in any form suitable for oral administration. For example, a nutritional supplement can typically be in a tablet, gel-cap, capsule, liquid, sachets, or syrup form.

Pharmaceutical Formulations

Also, disclosed herein are pharmaceutical formulations comprising the compositions disclosed herein. A suitable pharmaceutical formulation can comprise any of the disclosed compositions with a pharmaceutically acceptable carrier. For example, a pharmaceutical formulation can comprise composition comprising an oil (e.g. marine oil), wherein the composition has less than or equal to about 6 mg of cholesterol per gram of oil, a p-Anisidine value of less than or equal to 25, a Gardner color of less than or equal to 18, from about 0 to about 700 milligrams of DHA and/or EPA per gram of the composition (or a EPA:DHA wt. % ratio of from 0:70 to 70:0), less or equal to about 5 wt. % trans-fatty acids, and/or greater than or equal to about 97 wt. % triglycerides, and a pharmaceutically acceptable carrier. The disclosed pharmaceutical formulations can be used therapeutically or prophylactically.

By "pharmaceutically acceptable" is meant a material that is not biologically or otherwise undesirable, i.e., the material may be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Suitable carriers and their formulations are described in *Remington: The Science and Practice of Pharmacy*, $21^{st}$ ed., Lippincott Williams & Wilkins, Philiedalphia, Pa., 2005, which is incorporated by reference herein for its teachings of carriers and pharmaceutical formulations. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8 (e.g., from about 7 to about 7.5). Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, marine oils, and injectable organic esters such as ethyl oleate. Aqueous carriers include water, alcoholic/aqueous solutions, and emulsions or suspensions, including saline and buffered media. Parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives may also be present such as, for example, antimicrobials anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like can be desirable.

Pharmaceutical formulations for oral administration include, but are not limited to, powders or granules, suspensions or solutions in water or non-aqueous media, capsules, sachets, or tablets. Thickeners, flavorings, diluents, emulsifiers, dispersing aids, or binders can be desirable.

Some of the formulations can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanol amines.

Delivery Devices

Any of the compositions described herein can be incorporated into a delivery device. Examples of delivery devices include, but are not limited to, microcapsules, microspheres, nanospheres or nanoparticles, liposomes, noisome, nanoerythrosome, solid-liquid nanoparticles, gels, gel capsules, tablets, lotions, creams, sprays, emulsions, or powders. Other examples of delivery devices that are suitable for non-oral administration include pulmospheres. Examples of particular delivery devices useful herein are described below.

The disclosed compounds can be incorporated into liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The disclosed compositions in liposome form can contain, in addition to a compositions disclosed herein, stabilizers, preservatives, excipients, and the like. Examples of suitable lipids are the phospholipids and the phosphatidyl cholines (lecithins), both natural and synthetic. Methods of forming liposomes are known in the art. See, e.g., Prescott, Ed., *Methods in Cell Biology*, Volume XIV, Academic Press, New York, p. 33 et seq., 1976, which is hereby incorporated by reference herein for its teachings of liposomes and their preparation.

In other examples, the liposomes can be cationic liposomes (e.g., DOTMA, DOPE, DC cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see e.g., Brigham et al., *Am. J. Resp. Cell. Mol. Biol.* 1989, 1: 95-100; Felgner et al., *Proc. Natl. Acad. Sci. USA* 1987, 84: 7413-7; and U.S. Pat. No. 4,897,355, which are incorporated by reference herein for their teachings of liposomes. As one example, delivery can be via a liposome using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. Liposomes where the diffusion of the compound or delivery of the compound from the liposome is designed for a specific rate or dosage can also be used.

As described herein, niosomes are delivery devices that can be used to deliver the disclosed compositions. Noisomes are multilamellar or unilamellar vesicles involving non-ionic surfactants. An aqueous solution of solute is enclosed by a bilayer resulting from the organization of surfactant macromolecules. Similar to liposomes, noisomes are used in targeted delivery of, for example, anticancer drugs, including methotrexate, doxorubicin, and immunoadjuvants. They are generally understood to be different from transferosomes, vesicles prepared from amphiphilic carbohydrate and amino group containing polymers, e.g., chitosan.

As described herein, nanoerythrosomes are delivery devices that can be used to deliver the disclosed compositions. Nanoerythrosomes are nano-vesicles made of red blood cells via dialysis through filters of defined pore size. These vesicles can be loaded with a diverse array of biologically active molecules, including proteins and the compositions disclosed herein. They generally serve as ideal carriers for antineoplastic agents like bleomycin, actinomycin D, but can be used for steroids, other lipids, etc.

Artificial red blood cells are further delivery devices that can be used to deliver the disclosed compositions. Artificial red blood cells can be generated by interfacial polymerization and complex emulsion methods. Generally, the "cell" wall is made of polyphtaloyl L-lysine polymer/polystyrene and the core is made of a hemoglobin solution from sheep hemolysate. Hemoglobin loaded microspheres typically have particle sizes of from about 1 to about 10 mm. Their size, flexibility, and oxygen carrying capacity is similar to red blood cells.

Solid-lipid nanoparticles are other delivery devices that can be used to deliver the disclosed compositions. Solid-lipid nanoparticles are nanoparticles that are dispersed in an aqueous surfactant solution. They are comprised of a solid hydrophobic core having a monolayer of a phospholipid coating and are usually prepared by high-pressure homogenization techniques. Immunomodulating complexes (ISCOMS) are examples of solid-lipid nanoparticles. They are cage-like 40 nm supramolecular assemblies comprising of phospholipid, cholesterol, and hydrophobic antigens and are used mostly as immunoadjuvants. For instance, ISCOMs are used to prolong blood-plasma levels of subcutaneously injected cyclosporine.

Microspheres and micro-capsules are yet other delivery devices that can be used to deliver the disclosed compositions. In contrast to liposomal delivery systems, microspheres and micro-capsules typically do not have an aqueous core but a solid polymer matrix or membrane. These delivery devices are obtained by controlled precipitation of polymers, chemical cross-linking of soluble polymers, and interfacial polymerization of two monomers or high-pressure homogenization techniques. The encapsulated compound is gradually released from the depot by erosion or diffusion from the particles. Successful formulations of short acting peptides, such as LHRH agonists like leuprorelin and triptoreline, have been developed. Poly(lactide co-glycolide (PLGA) microspheres are currently used as monthly and three monthly dosage forms in the treatment of advanced prostate cancer, endometriosis, and other hormone responsive conditions. Leuprolide, an LHRH superagonist, was incorporated into a variety of PLGA matrices using a solvent extraction/evaporation method. As noted, all of these delivery devices can be used with the disclosed compositions.

Pulmospheres are still other examples of delivery devices that can be used herein. Pulmospheres are hollow porous particles with a low density (less than about 0.1 g/mL). Pulmospheres typically have excellent re-dispersibility and are usually prepared by supercritical fluid condensation technology. Co-spray-drying with certain matrices, such as carbohydrates, human serum albumin, etc., can improve the stability of proteins and peptides (e.g., insulin) and other biomolecules for pulmonary delivery. This type of delivery could be also accomplished with micro-emulsions and lipid emulsions, which are ultra fine, thin, transparent oil-in-water (o/w) emulsions formed spontaneously with no significant input of mechanical energy. In this technique, an emulsion can be prepared at a temperature, which must be higher than the phase inversion temperature of the system. At elevated temperature the emulsion is of water-in-oil (w/o) type and as it cools at the phase inversion temperature, this emulsion is inverted to become o/w. Due to their very small inner phase, they are extremely stable and used for sustained release of steroids and vaccines. Lipid emulsions comprise a neutral lipid core (i.e., triglycerides) stabilized by a monolayer of amphiphilic lipid (i.e., phospholipid) using surfactants like egg lecithin triglycerides and miglyol. They are suitable for passive and active targeting.

There are other oral delivery systems under investigation that are based on osmotic pressure modulation, pH modulation, swelling modulation, altered density and floating systems, mucoadhesiveness etc. These formulations and time-delayed formulations to deliver drugs in accordance with circadian rhythm of disease that are currently in use or investigation can be applied for delivery of the disclosed compositions.

Microcapsules

In one aspect disclosed herein, the disclosed compositions can be incorporated into microcapsules. For example, the microcapsule can comprise an agglomeration of primary microcapsules and disclosed compositions, each individual primary microcapsule having a primary shell, wherein the disclosed compositions are encapsulated by the primary shell, wherein the agglomeration is encapsulated by an outer shell. These microcapsules are referred to herein as "multi-core microcapsules."

In another aspect, described herein are microcapsules comprising a composition disclosed herein, a primary shell, and a secondary shell, wherein the primary shell encapsulates the disclosed composition, and the secondary shell encapsulates the loading substance and primary shell. These microcapsules are referred to herein as "single-core microcapsules.

Optionally, other loading substances can be encapsulated with the disclosed compositions. This additional loading substance can be any substance that is not entirely soluble in the aqueous mixture. In one aspect, the loading substance is a solid, a hydrophobic liquid, or a mixture of a solid and a hydrophobic liquid. In another aspect, the loading substance comprises a grease, an oil, a lipid, a drug (e.g., small molecule), a biologically active substance, a nutritional supplement (e.g., vitamins), a flavor compound, or a mixture thereof. Examples of oils include, but are not limited to, animal oils (e.g., fish oil, marine mammal oil, etc.), vegetable oils (e.g., canola or rapeseed), mineral oils, derivatives thereof or mixtures thereof. The loading substance can be a purified or partially purified oily substance such as a fatty acid, a triglyceride or ester thereof, or a mixture thereof. In another aspect, the loading substance can be a carotenoid (e.g., lycopene), a satiety agent, a flavor compound, a drug (e.g., a water insoluble drug), a particulate, an agricultural chemical (e.g., herbicides, insecticides, fertilizers), or an aquaculture ingredient (e.g., feed, pigment).

In one aspect, the loading substance can be an omega-3 fatty acid, as disclosed above, including derivatives thereof. Many types of derivatives of omega-3 fatty acids are well known in the art. Examples of suitable derivatives include, but are not limited to, esters, such as phytosterol esters, branched or unbranched $C_1$-$C_{30}$ alkyl esters, branched or unbranched $C_2$-$C_{30}$ alkenyl esters, or branched or unbranched $C_3$-$C_{30}$ cycloalkyl esters such as phytosterol esters and $C_1$-$C_6$ alkyl esters. Sources of oils can be derived from aquatic organisms (e.g., anchovies, capelin, Atlantic cod, Atlantic herring, Atlantic mackerel, Atlantic menhaden, salmonids, sardines, shark, tuna, etc) and plants (e.g., flax, vegetables, etc) and microorganisms (e.g., fungi and algae).

In one aspect, the loading substance can contain an antioxidant. Examples of antioxidants include, but are not limited to, vitamin E, $CoQ_{10}$, tocopherols, lipid soluble derivatives of more polar antioxidants such as ascorbyl fatty acid esters (e.g. ascorbyl palmitate), plant extracts (e.g., rosemary, sage and oregano oils), algal extracts, and synthetic antioxidants (e.g., BHT, TBHQ, ethoxyquin, alkyl gallates, hydroquinones, tocotrienols).

A number of different polymers can be used to produce the shell layers of the single and multicore microcapsules. Examples of such polymers include, but are not limited to, a protein, a polyphosphate, a polysaccharide, or a mixture thereof. In another aspect, the shell material used to prepare the single- and multicore microcapsules further comprises In another aspect, the shell material used to prepare the single- and multicore microcapsules further comprises gelatin type A, gelatin type B, polyphosphate, gum arabic, alginate, chitosan, carrageenan, pectin, starch, modified starch, alfa-lactalbumin, beta-lactoglobumin, ovalbumin, polysorbiton, maltodextrins, cyclodextrins, cellulose, methyl cellulose, ethyl cellulose, hydropropylmethylcellulose, carboxymethylcellulose, milk protein, whey protein, soy protein, canola protein, albumin, chitin, polylactides, poly-lactide-co-glycolides, derivatized chitin, chitosan, poly-lysine, various inorganic-organic composites, or any mixture thereof. It is also contemplated that derivatives of these polymers can be used as well. In another aspect, the polymer can be kosher gelatin, non-kosher gelatin, Halal gelatin, or non-Halal gelatin.

In one aspect, one or more of the shell layers in the single and multicore microcapsules comprises gelatin having a Bloom number less than 50. This gelatin is referred to herein as "low Bloom gelatin." The Bloom number describes the gel strength formed at 10° C. with a 6.67% solution gelled for 18 hours. In one aspect, the low Bloom gelatin has a Bloom number less than 40, less than 30, less than 20, or less than 10. In another aspect, the gelatin has a Bloom number of 45, 40, 35, 30, 25, 20, 15, 10, 9, 8, 7, 6, 5, 4, 3, 2, 1, or 0, where any stated value can for an upper and/or lower endpoint as appropriate. In another aspect, the low Bloom gelatin is in both the primary shell and the outer shell of the multicore microcapsule. In one aspect, the low Bloom gelatin is gelatin type A. In another aspect, the low Bloom gelatin is gelatin type A produced by Kenney & Ross Ltd., R.R. #3 Shelburne, NS Canada. In another aspect, gelatin having a Bloom number of zero is in both the primary shell and the outer shell of the multicore microcapsule.

The material used to make the shells of the single- or multicore microcapsules can be a two-component system made from a mixture of two different types of polymers. For example, the material can be a complex coacervate between the polymer components. Complex coacervation is caused by the interaction between two oppositely charged polymers. In one aspect, the shell material used to produce the single and multicore microcapsules is composed of (1) low Bloom gelatin and (2) gelatin type B, polyphosphate, gum arabic, alginate, chitosan, carrageenan, pectin, carboxymethylcellulose, whey protein, soy protein, canola protein, albumin, or a mixture thereof. The molar ratio of the different polymers can vary. For example, the molar ratio of low Bloom gelatin to the other polymer component is from 1:5 to 15:1. For example, when low Bloom gelatin and polyphosphate are used, the molar ratio of low Bloom gelatin to polyphosphate is about 8:1 to about 12:1; when low Bloom gelatin and gelatin type B are used, the molar ratio is 2:1 to 1:2; and when low Bloom gelatin and alginate are used, the molar ratio is 3:1 to 8:1.

Processing aids can be included in the shell material (e.g., primary or outer shells). Processing aids can be used for a variety of reasons. For example, they may be used to promote agglomeration of the primary microcapsules, stabilize the emulsion system, improve the properties of the outer shells, control microcapsule size and/or to act as an antioxidant. In one aspect, the processing aid can be an emulsifier, a fatty acid, a lipid, a wax, a microbial cell (e.g., yeast cell lines), a clay, or an inorganic compound (e.g., calcium carbonate). Not wishing to be bound by theory, these processing aids can improve the barrier properties of the microcapsules. In one aspect, one or more antioxidants can be added to the shell material. Antioxidant properties are useful both during the process (e.g. during coacervation and/or spray drying) and in the microcapsules after they are formed (i.e. to extend shelf-life, etc). Preferably a small number of processing aids that perform a large number of functions can be used. In one aspect, the antioxidant can be a phenolic compound, a plant extract, or a sulphur-containing amino acid. In one aspect, ascorbic acid (or a salt thereof such as sodium or potassium ascorbate) can be used to promote agglomeration of the primary microcapsules, to control microcapsule size and to act as an antioxidant. The antioxidant can be used in an amount of about 100 ppm to about 12,000 ppm, or from about 1,000 ppm to about 5,000 ppm. Other processing aids such as, for example, metal chelators, can be used as well. For example, ethylene diamine tetraacetic acid can be used to bind metal ions, which can reduce the catalytic oxidation of the loading substance.

In one aspect, the primary microcapsules (primary shells) have an average diameter of about 40 nm to about 10 μm, 0.1 μm to about 10 μm, 1 μm to about 10 μm, 1 μm to about 8 μm, 1 μm to about 6 μm, 1 μm to about 4 μm, or 1 μm to about 2 μm, or 1 μm. In another aspect, the multicore microcapsules can have an average diameter of from about 1 μm to about 2000 μm, 20 μm to about 1000 μm, from about 20 μm to about 100 μm, or from about 30 μm to about 80 μm. In another aspect, the single-core microcapsules have an outer diameter of from 1 μm to 2,000 μm.

The microcapsules described herein generally have a combination of high payload and structural strength. For example, payloads of loading substance can be from 20% to 90%, 50% to 70% by weight, or 60% by weight of the single or multicore microcapsules.

In one aspect, the methods disclosed in U.S. Patent Application Publication No. 2003/0193102, which is incorporated by reference in its entirety, can be used to encapsulate the disclosed compositions. It is also contemplated that one or more additional shell layers can be placed on the outer shell of the single or multicore microcapsules. In one aspect, the techniques described in International Publication No. WO 2004/041251 A1, which is incorporated by reference in its entirety, can be used to add additional shell layers to the single and multicore microcapsules.

Targeted Delivery

The disclosed compositions can be targeted to a particular cell type, such as islets cells, via antibodies, receptors, or receptor ligands. The following references are examples of the use of this technology to target specific tissue (Senter et al., *Bioconjugate Chem.* 1991, 2: 447-51; Bagshawe, *Br. J. Cancer* 1989, 60: 275-81; Bagshawe et al., *Br. J. Cancer* 1988, 58: 700-3; Senter et al., *Bioconjugate Chem* 1993, 4: 3-9; Battelli et al., *Cancer Immunol. Immunother.* 1992, 35: 421-5; Pietersz and McKenzie, *Immunolog. Rev.* 1992, 129: 57-80; Roffler et al., *Biochem. Pharmacol.* 1991, 42: 2062-5). These techniques can be used for a variety of other specific cell types.

Foodstuffs

Also disclosed herein are foodstuffs comprising any of the disclosed compositions. By "foodstuff" is meant any article that can be consumed (e.g., eaten, drank, or ingested) by a subject. In one aspect, the microcapsules can be used as nutritional supplements to a foodstuff. For example, the microcapsules and emulsions can be loaded with vitamins, omega-3 fatty acids, and other compounds that provide health benefits. In one aspect, the foodstuff is a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar (e.g., white or brown), a sauce, a gravy, a syrup, a nutritional bar, a beverage, a dry beverage powder, a jam or jelly, a fish product, or pet companion food. In another aspect, the foodstuff is bread, tortillas, cereal, sausage, chicken, ice cream, yoghurt, milk, salad dressing, rice bran, fruit juice, a dry beverage powder, rolls, cookies, crackers, fruit pies, or cakes.

Methods of Use

The disclosed compositions also have a wide variety of uses. For example, the disclosed compositions (including the nutritional supplements, pharmaceutical formulations, delivery devices, and foodstuffs) can be used as a source of fatty acids (e.g., PUFA's like omega-3 fatty acids), lowering triglycerides and influencing diabetes related biochemistry.

In one particular example, disclosed herein are methods of supplementing omega-3 fatty acids in a subject by administering an effective amount of a composition disclosed herein, wherein the composition comprises an omega-3 fatty acid. In another example, disclosed herein are methods of lowering cholesterol levels, triglyceride levels, or a combination thereof in a subject by administering an effective amount of a composition disclosed herein.

In the disclosed methods, the compositions can be any of the compositions disclosed herein. Also, the disclosed compositions can be used neat or in combination with some other component. For example, the disclosed compositions can be used in; the disclosed methods in the form of any of the nutritional supplements disclosed herein. In another example, the disclosed compositions can be used in the disclosed methods in the form of any of the pharmaceutical formulations disclosed herein. In still another example, the disclosed compositions can be incorporated in any of the delivery devices disclosed herein, or incorporated into any foodstuff disclosed herein and used in the disclosed methods.

It is contemplated that the methods disclosed herein can be accomplished by administering various forms of the disclosed compositions. For example, one can administer any of the pharmaceutical formulations with any of the foodstuffs disclosed herein. In another example, one can administer a microcapsule with any of the nutritional supplements disclosed herein. In yet another example, one can administer any of the pharmaceutical formulations with any of the delivery devices and nutritional supplement disclosed herein, and the like.

Dosage

When used in the above described methods or other treatments, or in the nutritional supplements, pharmaceutical formulations, delivery devices, or foodstuffs disclosed herein, an "effective amount" of one of the disclosed compositions can be employed in pure form or, where such forms exist, in pharmaceutically acceptable salt form, and with or without a pharmaceutically acceptable excipient, carrier, or other additive.

The specific effective dose level for any particular subject will depend upon a variety of factors including the disorder being treated and the severity of the disorder; the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts. For example, it is well within the skill of the art to start doses of the composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose.

The dosage can be adjusted by the individual physician or the subject in then event of any counterindications. Dosage can vary, and can be administered in one or more dose administrations daily, for one or several days. Guidance can be found in the literature for appropriate dosages for given classes of pharmaceutical products.

Administration and Delivers

In one aspect, disclosed herein are uses of a delivery device to deliver a disclosed compositions to a subject. Further, disclosed are methods for delivering a disclosed compositions to a subject by administering to the subject any of the nutritional supplements, pharmaceutical formulations, delivery devices, and/or foodstuffs disclosed herein.

The disclosed compositions (including nutritional supplements, microcapsules, delivery devices, and pharmaceutical formulations) can be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, temperatures, pressures, and other reaction ranges and conditions that can be used to optimize the product purity and yield obtained from the described process. Only reasonable and routine experimentation will be required to optimize such process conditions.

Certain materials, compounds, compositions, and components disclosed herein can be obtained commercially or readily synthesized using techniques generally known to those of skill in the art. For example, the starting materials and reagents used in preparing the disclosed compositions are either available from commercial suppliers such as Ocean Nutrition Canada, Ltd. (Dartmouth, Canada), Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Example 1

The following examples use TRISYL™, a TRISYL™/clay combination, and clay alone to remove cholesterol in TG 18/12. TG 18/12 is a triglyceride marine oil with about 18 wt. % EPA and about 12 wt. % DHA. These examples use crude TG 18/12, lot #3929, with a cholesterol level of 6.5 mg/g as the starting oil. Different crude TG 18/12 oils can have different cholesterol contents. The cholesterol removal conditions disclosed herein can be adjusted for different oils. For example, crude TG 18/12, lot #2755, has 4.3 mg/g cholesterol, and thus a milder treatment can be used to reduce cholesterol to below 1 mg/g.

Adsorbents

TRISYL™ was first tested for cholesterol removal at 80° C. and showed a better effect than that of clay. However, TRISYL™ does not remove color well. A TRISYL™/clay combination was tested for cholesterol removal as well as bleaching. The amounts of TRISYL™/clay (1:1) in marine oil were 10% or above (up to 20%) at 180° C. and the cholesterol level could be reduced to below 1 mg/g (e.g. 0.15 mg/g). Using from 5 to 6% TRISYL™/clay, cholesterol was reduced to from 1.0 to 2.0 mg/g at 180° C.

At high temperatures, clay showed a significantly increased effect to reduce cholesterol. At 80° C., 3% clay reduced about 15% cholesterol in TG 18/12 (lot #3929), while at 180° C., 3% clay removed more than 60% cholesterol in the oil. Using 6% clay in the fish oil at 190° C. for 10-20 minutes reduced cholesterol to from 0.5 to 0.8 mg/g. It seemed 10-minute treatment was enough to produce cholesterol free oil, although most of the treatments were tested for 20 minutes. For milder conditions, treatment time can be increased to achieve cholesterol free compositions.

Color

The high temperature treatment under vacuum did not darken the oil color. The color of the oil after the treatment was lighter than that after a normal bleaching procedure (3% clay at 80° C.). While not wishing to be bound by theory, it is believed that one reason for the improved color is that a higher amount of clay is used in the de-cholesterol procedure.

p-Anisidine Value

Crude TG18/12 (lot #3929) oil had a p-Anisidine value of 20. A normal bleaching with 3% clay and 80° C. reduced the value to 12. Oil samples treated at high temperature with clay and TRISYL™ had lower p-Anisidine values (e.g., from 3 to 7) (see Table 4).

TABLE 4

Effect of treatments on p-Anisidine values and cholesterol contents

| Sample information | Cholesterol (mg/g) | p-Anisidine |
|---|---|---|
| TG18/12, lot #3929, crude oil (herein "3929 Crude Oil") | 6.55 | 20.46 |
| Clay:3929 Crude Oil 3:100, 80° C., 60 min | 5.45 | 12.44 |
| Clay:Trisyl:3929 Crude Oil 7:7:100, 180° C., 20 min, | 0.68 | 3.89 |
| Clay:Trisyl:3929 Crude Oil 1:1:10, 180° C., 20 min | 0.15 | 4.19 |
| Clay:Trisyl:3929 Crude Oil 6:6:100, 180° C., 20 min | 0.91 | 3.60 |
| Clay:3929 Crude Oil 7:100, 180° C., 20 min | 0.69 | 5.42 |

TABLE 4-continued

Effect of treatments on p-Anisidine values and cholesterol contents

| Sample information | Cholesterol (mg/g) | p-Anisidine |
|---|---|---|
| Clay:3929 Crude Oil 6:100, 190° C., 20 min | 0.76 | 5.82 |
| Clay:3929 Crude Oil 5:100, 200° C., 20 min | 1.16 | 6.64 |
| Clay:3929 Crude rude Oil 6:100, 200° C., 10 min | 0.45 | 5.98 |
| Clay:3929 Crude Oil 6:100, 210° C., 20 min | 0.18 | 7.14 |
| Clay:3929 Crude Oil 6:100, 190-200° C., 20 min | 0.45 | 6.93 |

EPA and DHA

High temperature can destroy EPA and DHA, especially in the presence of absorbents. As the temperature and time increased, the loss of EPA and DHA increased (see Table 5). There are about 6 to 7 wt. % EPA and 8 to 9 wt. % DHA losses in the cholesterol free oil (e.g., <1 mg/g) using the disclosed methods. To minimize losses of EPA and DHA, a shorter treatment time can be used.

TABLE 5

Effect of treatments on EPA, DHA, and cholesterol contents

| Sample information | Cholesterol (mg/g) | EPA (mg/g) | DHA (mg/g) |
|---|---|---|---|
| 3929 Crude Oil | 6.55 | 168.48 | 117.85 |
| Clay:3929 Crude Oil 7:100, 180° C., 20 min | 0.69 | 157.07 | 108.29 |
| Clay:3929 Crude Oil 6:100, 190° C., 20 min | 0.76 | 157.38 | 108.01 |

TABLE 5-continued

Effect of treatments on EPA, DHA, and cholesterol contents

| Sample information | Cholesterol (mg/g) | EPA (mg/g) | DHA (mg/g) |
|---|---|---|---|
| Clay:3929 Crude Oil 5:100, 200° C., 20 min | 1.16 | 157.09 | 108.45 |
| Clay:3929 Crude Oil 6:100, 200° C., 10 min | 0.45 | 153.85 | 105.10 |
| Clay:3929 Crude Oil 6:100, 190-200° C., 20 min | 0.45 | 152.49 | 103.07 |
| Clay:3929 Crude Oil 6:100, 210° C., 20 min | 0.18 | 123.39 | 78.97 |

Lipid Class

The starting TG 18/12, lot #3929, oil has over 98 wt. % of triglycerides and small amount of diglycerides. After the disclosed treatments, no breakdown of triglycerides occurred. The diglyceride content was reduced by the treatments. TRISYL™ and clay can absorb compounds (e.g., polar lipids) as well as impurities.

TABLE 6

Effect of treatments on tri-, di-, and mono-glyceride contents (TG, DG, and MG, respectively)

| Sample information | TG (%) | DG (%) | MG (%) |
|---|---|---|---|
| 3929 Crude Oil | 98.6 | 1.4 | 0.0 |
| Clay:3929 Crude Oil 1:1:10, 180° C., 20 min | 100 | 0.0 | 0.0 |
| Clay:3929 Crude Oil 6:100, 200° C., 10 min | 99.0 | 1.0 | 0.0 |
| Clay:3929 Crude Oil 6:100, 190-200° C., 20 min | 99.2 | 0.8 | 0.0 |

TABLE 7

Cholesterol removal effects of clay and TRISYL ™

| Sample information | Cholesterol (mg/g) |
|---|---|
| TG18/12, lot #4381, crude oil (herein "4381 Crude Oil") | 4.25 |
| Trisyl:4381 Crude Oil 1:10, 80° C., 60 min | 2.81 |
| Clay:4381 Crude Oil 1:1:10, 80° C., 50 min, 180° C., 10 min | 0.73 |
| Repeated cholesterol analysis | 0.71 |
| 3929 Crude Oil | 6.34 |
| Clay:Trisyl:3929 Crude Oil 1:1:10, 180° C., 20 min | 0.71 |
| Repeated cholesterol analysis | 0.70 |
| 4381 Crude Oil | 4.30 |
| Trisyl:4381 Crude Oil 1:10, 180° C., 20 min, (>80° C. for ~45 min) | 1.88 |
| Clay:Trisyl:4381 Crude Oil 1:1:10, 180° C., 20 min, (>80° C. for ~45 min) | 0.21 |
| Clay:4381 Crude Oil 1:10, 180 C., 20 min, (>80° C. for ~45 min) | 0.09 |
| Repeated analysis | 0.08 |
| Clay:Trisyl:3604 Crude Oil 1:1:10, 180° C., 20 min, (>80° C. for ~45 min) | 0.84 |
| Trisyl:3604 Crude Oil 1:20, 180° C., 40 min, (>80° C. for ~45 min) | 1.88 |
| 3929 Crude Oil | 6.50 |
| Clay:Trisyl:3929 Crude Oil 1:1:20, 180° C., 20 min, (>80° C. for ~45 min) | 1.80 |
| Clay:Trisyl:3929 Crude Oil 1:1:10, 130° C., 20 min, (>80° C. for ~45 min) | 2.44 |
| Clay:Trisyl:3929 Crude Oil 3:3:100, 180° C., 20 min, (>80° C. for ~45 min) | 1.00 |
| 3929 Crude Oil, bottle A | 6.55 |
| Clay:Trisyl:3929 Crude Oil (bottle A) 3:3:100, 180° C., 20 min, (>80° C. for ~45 min) | 1.89 |
| Clay:Trisyl:3929 Crude Oil (bottle A) 1:1:20, 130° C., 40 min, (>80° C. for ~60 min) | 2.52 |
| Clay:3929 Crude Oil (bottle A) 1:20, 180° C., 20 min, (>80° C. for ~50 min) | 1.22 |
| Clay:Trisyl:3929 Crude Oil (bottle A) oil 7:7:100, 180° C., 20 min, (>80° C. for ~45 min) | 0.68 |
| Clay:Trisyl:3929 Crude Oil (bottle A) 1:1:10, 160° C., 20 min, (>80° C. for ~45 min) | 1.18 |
| Clay:Trisyl:3929 Crude Oil (bottle A) 1:1:10, 180° C., 20 min, (>80° C. for ~45 min) | 0.15 |
| Clay:Trisyl:3929 Crude Oil (bottle A) 6:6:100, 180° C., 20 min, (>80° C. for ~45 min) | 0.91 |
| Clay:Trisyl:3929 Crude Oil (bottle A) 1:1:10, 180° C., 10 min, (>80° C. for ~35 min) | 0.59 |
| Clay:Trisyl:3929 Crude Oil (bottle A) 1:1:20, 160° C., 20 min, (>80° C. for ~45 min) | 2.04 |
| Clay:Trisyl:3929 Crude Oil (bottle A) 3:3:100, 180° C., 20 min, (>80° C. for ~45 min) | 1.07 |
| Clay:Trisyl:3929 Crude Oil (bottle A) 1:1:10, 180° C., 20 min, (>80° C. for ~45 min) | 0.34 |

TABLE 7-continued

Cholesterol removal effects of clay and TRISYL ™

| Sample information | Cholesterol (mg/g) |
|---|---|
| Clay:Trisyl:3929 Crude Oil (bottle A) 1:1:20, 180° C., 20 min, (>80° C. for ~45 min) | 0.74 |
| 3929 Crude Oil | 6.40 |
| Clay:Trisyl:3929 Crude Oil 2:3:100, 180° C., 20 min, (>80° C. for ~45 min) | 2.11 |
| Clay:Trisyl:3929 Crude Oil (A) 2:3:100, 180° C., 20 min, (>80° C. for ~45 min) | 1.43 |
| Clay:Trisyl:3929 Crude Oil 1:1:40, 180° C., 20 min, (>80° C. for ~45 min) | 1.50 |
| Clay:Trisyl:oil from sample immediately above 1:1:40, 180° C., 20 min, (>80° C. for ~45 min) | 1.06 |
| Clay:Trisyl:3929 Crude Oil 2:3:100, 160° C., 20 min, (>80° C. for ~45 min) | 2.32 |
| Clay:Trisyl:oil from sample immediately above 2:3:100, 160° C., 20 min, (>80° C. for ~45 min) | 1.93 |
| Clay:3929 Crude Oil 6:100, 180° C., 20 min, (>80° C. for ~45 min) | 1.19 |
| Clay:3929 Crude Oil 6:100, 160° C., 20 min, (>80° C. for ~45 min) | 1.69 |
| Clay:3929 Crude Oil 3:100, 180° C., 20 min, (>80° C. for ~45 min) | 2.33 |
| Clay:oil from sample immediately above 3:100, 180° C., 20 min, (>80° C. for ~45 min) | 1.51 |
| Clay:3929 Crude Oil 3:100, 80° C., 60 min, | 5.45 |
| Clay:3929 Crude Oil 7:100, 180° C., 20 min, (>80° C. for ~45 min) | 0.69 |
| Clay:3929 Crude Oil 7:100, 170° C., 20 min, (>80° C. for ~45 min) | 1.37 |
| Clay:3929 Crude Oil 5:100, 190° C., 20 min, (>80° C. for ~45 min) | 1.07 |
| Clay:3929 Crude Oil 6:100, 190° C., 20 min, (>80° C. for ~45 min) | 0.76 |
| Clay:3929 Crude Oil 5:100, 200° C., 20 min, (>80° C. for ~45 min) | 1.16 |
| Clay:3929 Crude Oil 5:100, 190° C., 20 min, (>80° C. for ~45 min) | 1.15 |
| Clay:3929 Crude Oil 6:100, 200° C., 10 min, (>80° C. for ~35 min) | 0.45 |
| Clay:3929 Crude Oil 6:100, 210° C., 20 min, (>80° C. for ~45 min) | 0.18 |
| Clay:3929 Crude Oil 6:100, 190-200° C., 20 min, (>80° C. for ~45 min) | 0.45 |
| TG18/12, lot #2755, crude oil (herein "2755 Crude Oil") | 4.31 |
| Clay:2755 Crude Oil 6:100, 180° C., 20 min, (>80° C. for ~45 min) | 0.73 |

Results

At medium temperature (about 80° C.), TRISYL™ showed a better effect to remove cholesterol from the oil than that of clay. The combination of TRISYL™ and clay reduced up to 56 wt. % of cholesterol in the oil but did not reduce the cholesterol level below 2 mg/g. At higher temperatures (e.g., greater than about 180° C.), clay showed a significantly increased effect to remove cholesterol. Clay alone or a combination of TRISYL™/clay were found to be able to remove up to 98 wt. % of cholesterol. The conditions of using 5 wt. % clay at 180 to 190° C. were found to be able to reduce cholesterol levels to 1.0 to 1.5 mg/g. The conditions of using 6 to 7 wt. % clay at 180 to 190° C. were found to be able to reduce cholesterol level to below 1.0 mg/g.

About 6.5% EPA and about 8.5% DHA were lost using these methods. Also de-cholesterol samples had lower p-Anisidine values as compared to that of the starting oil. Further, lipid class analysis showed that the treatments reduced mono- and di-glycerides.

Example 2

Seven TG 18/12 oils were tested for milder conditions. They were crude oils with lot numbers #3929, #2755 and #3985, and steam deodorized oils with lot numbers #5147, #4254 (two bottles with different cholesterol contents), and #5139. These oils are identified respectively herein as 3929 Crude Oil, 2755 Crude Oil, 3985 Crude Oil, 5147 Crude Oil, 4254 Crude Oil (Bottle A and Bottle B), and 5139 Crude Oil.

The temperatures were chosen from 140 to 160° C. based on the previous experiment results. Temperature can be a factor to remove cholesterol in fish oil using clay. Table 8 shows how temperatures affect cholesterol removal with 6% clay.

TABLE 8

Effect of temperatures on cholesterol removal

| Sample information | Cholesterol (mg/g) |
|---|---|
| 3929 Crude Oil | 6.40 |
| Clay:3929 Crude Oil 6:100, 160° C., 20 min | 1.69 |
| Clay:3929 Crude Oil 6:100, 180° C., 20 min | 1.19 |
| Clay:3929 Crude Oil 6:100, 190° C., 20 min | 0.76 |
| Clay:3929 Crude Oil 6:100, 200° C., 10 min | 0.45 |
| Clay:3929 Crude Oil 6:100, 210° C., 20 min | 0.18 |

Table 9 shows the results at 140° C. for 20 min. The cholesterol levels were slightly above 2 mg/g after the treatments. For normal fish oils (with cholesterol level between 4-7 mg/g), the cholesterol contents after the treatment were most likely to be 2.0 to 2.5 mg/g. In order to reduce cholesterol level below 2 mg/g, increase of treatment time or temperature can be used.

TABLE 9

Cholesterol removal at about 140° C.

| Sample information | Cholesterol (mg/g) |
|---|---|
| 2755 Crude Oil | 5.43 |
| Clay:2755 Crude Oil 6:100, 140° C., 20 min | 2.16 |
| Clay:2755 Crude Oil 6:100, 140° C., 20 min | 2.25 |
| Clay:2755 Crude Oil 5:100, 140-150° C., 20 min | 2.14 |
| Clay:2755 Crude Oil 5:100, 140° C., 20 min | 2.25 |
| Clay:2755 Crude Oil 6:100, 150° C., 20 min | 2.05 |
| Clay:2755 Crude Oil 6:100, 150° C., 20 min | 2.10 |

After treatment at 160° C., the cholesterol contents in most of the fish oil tested (six of the seven oils) were below 2 mg/g (see Table 10). To prevent damage of fish oil, a 20 minute treatment time was chosen. For relatively mild conditions (140 to 160° C.), the treatment time could be increased to 40 to 60 minutes, which can further reduce cholesterol levels.

TABLE 10

Cholesterol removal at 160° C. with 6% clay

| Sample information | Cholesterol (mg/g) |
|---|---|
| 3929 Crude Oil | 6.40 |
| Clay:3929 Crude Oil 6:100, 160° C., 20 min | 1.69 |
| 2755 Crude Oil | 5.43 |
| Clay:2755 Crude Oil 6:100, 160° C., 20 min | 1.96 |
| 5147 Crude Oil (which is steam deodorized) | 5.25 |
| Clay:5147 Crude Oil 6:100, 160 C., 20 min | 1.97 |
| 4254 Crude Oil Bottle A (which is steam deodorized) | 5.06 |
| Clay:4254 Crude Oil Bottle A 6:100, 160° C., 20 min | 1.91 |
| 4254 Crude Oil Bottle B (which is steam deodorized) | 5.55 |
| Clay:4254 Crude Oil Bottle B 6:100, 160° C., 20 min | 1.96 |
| 5139 Crude Oil (which is steam deodorized) | 5.18 |
| Clay:5139 Crude Oil 6:100, 160° C., 20 min | 1.98 |
| 3985 Crude Oil | 7.11 |
| Clay:3985 Crude Oil 6:100, 160° C., 20 min | 2.89 |

The disclosed methods also served as bleaching procedures which produced lighter oil compared to that of normal bleaching procedure. High temperature bleaching did not show negative effects on the fish oil color.

Trans Fatty Acid

Trans-fatty acid contents in the fish oils before and after de-cholesterol procedure were tested. The oils were transferred into fatty acid methyl esters (FAMEs) and analyzed for trans-fatty acids. Ethyl EPA standard (all cis-EPA) was also transesterified into its FAME, to monitor how much trans-fatty acid might be produced during the transesterification. The results (Table 11) are based on area percentage (not quantified).

TABLE 11

Trans fatty acids in fish oils before and after treatment

| Sample | Trans EPA | Trans EPA (rep.) | Trans DHA | Trans DHA (rep.) |
|---|---|---|---|---|
| 3985 Crude Oil | 1.2 | 1.2 | 1.1 | 1.5 |
| After 160° C., 6% clay treatment | 1.2 | 1.4 | 1.4 | 1.5 |
| 5147 Crude Oil (which is steam deodorized) | 5.7 | 5.1 | 5.9 | 5.8 |
| After 160 C., 6% clay treatment | 7.4 | 5.9 | 7.6 | 7.1 |

Crude TG 18/12 oil, lot #3985, does not have much trans-fatty acids, while steam deodorized oil has a higher amount of trans-fatty acids. The disclosed procedures can be used before Steam deodorization.

For the crude oil, the disclosed procedures did not greatly increase trans-fatty acids. But for the steam deodorized oil, after the disclosed treatments, trans-fatty acids increase significantly. While not wishing to be bound by theory, it is believed that the steam deodorization produce itself increases trans-fatty acids and makes the oil vulnerable to the following treatments.

TABLE 12

Cholesterol removal results with clay

| Sample information | Cholesterol (mg/g) |
|---|---|
| 3929 Crude Oil | 6.40 |
| Clay:3929 Crude Oil 6:100, 160° C., 20 min | 1.69 |
| Clay:3929 Crude Oil 6:100, 180° C., 20 min | 1.19 |
| Clay:3929 Crude Oil 6:100, 190° C., 20 min | 0.76 |
| Clay:3929 Crude Oil 6:100, 200° C., 10 min | 0.45 |
| Clay:3929 Crude Oil 6:100, 210° C., 20 min | 0.18 |
| 2755 Crude Oil | 5.43 |
| Clay:2755 Crude Oil 6:100, 140° C., 20 min | 2.16 |
| Clay:2755 Crude Oil 6:100, 140° C., 20 min | 2.25 |
| Clay:2755 Crude Oil 6:100, 150° C., 20 min | 2.05 |
| Clay:2755 Crude Oil 6:100, 160° C., 20 min | 1.96 |
| Clay:2755 Crude Oil 6:100, 180° C., 20 min | 0.73 |
| 3985 Crude Oil, Bottle A | 7.15 |
| 3985 Crude Oil, Bottle B | 7.11 |
| Clay:3985 Crude Oil Bottle A 6:100, 140° C., 20 min | 3.22 |
| Clay:3985 Crude Oil Bottle A 6:100, 140° C., 20 min | 3.19 |
| Clay:3985 Crude Oil Bottle A 6:100, 160° C., 20 min | 2.89 |
| Clay:3985 Crude Oil Bottle B 6:100, 170° C., 20 min | 2.61 |
| Clay:3985 Crude Oil Bottle A 6:100, 170° C., 20 min | 2.34 |
| 5147 Crude Oil (which is steam deodorized) | 5.25 |
| 5147 Crude Oil repeat | 5.35 |
| Clay:5147 Crude Oil 6:100, 160° C., 20 min | 1.97 |
| Clay:5147 Crude Oil 5:100, 160° C., 20 min | 2.10 |
| 4254 Crude Oil Bottle A (which is steam deodorized) | 5.06 |
| Clay:4254 Crude Oil Bottle A 5:100, 160° C., 20 min | 1.95 |
| Clay:4254 Crude Oil Bottle A 6:100, 160° C., 20 min | 1.91 |
| 4254 Crude Oil Bottle B (which is steam deodorized) | 5.55 |
| Clay:4254 Crude Oil Bottle B 6:100, 160° C., 20 min | 1.96 |
| Clay:4254 Crude Oil Bottle B 5:100, 160° C., 20 min | 2.00 |
| 5139 Crude Oil (which is steam deodorized) | 5.18 |
| Clay:5139 Crude Oil 6:100, 160° C., 20 min | 1.98 |
| Clay:5139 Crude Oil 5:100, 160° C., 20 min | 2.06 |

Example 3

The effects of high-temperature-bleaching on oil qualities, cholesterol reduction, changes of EPA/DHA ratios and amounts, changes in trans-fatty acids, color, and oxidative stability were tested. Oxidative stability can be measured by well known methods, such as the Active Oxygen Method (AOM) and Oxygen Stability Index (OSI). These methods measure the extent of oxidation to provide an indication of the point at which oxidative rancidity occurs. Suitable methods form measuring oxidative stability can involve the use of the Oxidation Stability Instrument (available from Omnion Inc., Rockland, Mass.) and the Rancimat (available from Brinkman Instruments, Des Plaines, Ill.). These instruments measure the changes in conductivity caused by ionic volatile organic acids. The end point is selected as the point at which the rapid rise in conductance begins (i.e., the oxidative stability induction time).

TG oil, lot #8823, which was alkaline refined, was obtained from Mulgrave and Englehard clay. The processing temperature was at 150° C. 60 g of oil was mixed with 3 g clay. The mixture was placed under vacuum, stirred, and heated to 150° C. The mixture was allowed to continue stirring at 150° C. for 30 minutes. After cooling to 50° C. (about 40 min), the vacuum was broken with nitrogen. The mixture was then filtered through filtration paper.

TABLE 13

Effect of temperatures on cholesterol removal and oil qualities

| Sample processing | Cholesterol (mg/g) | Oxidative stability induction time (h) | EPA/DHA | Trans (wt. %) | Color (Gardner) |
|---|---|---|---|---|---|
| 8823 Crude Oil | 7.05 | 0.65 | 158/139 | | 11.5 yellow/brown |
| 30 min at 140° C. | 1.79 | 1.40 | | | |
| 30 min at 140° C. double bleaching each with 5% clay | 1.57 | 1.20 | | | |
| 45 min at 140° C. | 1.70 | 1.13 | | 1.5 | |
| 45 min at 140° C. double bleaching each with 5% clay | 1.15 | 1.20 | | | |
| 30 min at 150° C. | 1.73 | 1.10 | 151/142 | 1.3 | |
| 30 min at 150° C. | 1.74 | 1.05 | | 1.2 | |
| 30 min at 150° C. double bleaching each with 5% clay | 1.23 | 0.90 | | | |
| 30 min at 150° C. double bleaching each with 5% clay | 0.83 | 0.85 | 144/137 | 1.8 | |
| 45 min at 150° C. | 1.47 | 1.00 | 150/142 | 1.2 | 3.5 very light yellow |
| 45 min at 150° C. | 1.25 | 0.90 | | | 4.0 |
| 30 min at 160° C. | 1.70 | 1.15 | | 1.3 | |
| 30 min at 160° C. | 1.60 | 0.75 | | 1.3 | |
| 20 min at 180° C. | 1.28 | 0.80 | | 2.4 | |
| 20 min at 180° C. | 0.63 | 0.55 | | 2.4 | |

The starting oil (lot #8823) has a typical cholesterol level of 7 mg/g. The disclosed procedures were able to reduce the level to below 2.0 mg/g. The higher or longer the temperature or processing time, the lower the cholesterol level. The oxidative stability induction time of the oils treated increased.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for preparing a composition, comprising:
   a. contacting an oil with an adsorbent comprising clay to provide a mixture, wherein the clay is present in an amount of from about 5 to about 7 wt. %, based on the weight of the oil;
   b. heating the mixture to from about 150° C. to about 200° C.; and
   c. removing the adsorbent from the mixture, to provide the composition.

2. The method of claim 1, wherein heating is performed for at least 1 minute.

3. The method of claim 1, wherein heating is performed for at least 20 minutes.

4. The method of claim 1, wherein the mixture is heated to from about 150 to about 170° C.

5. The method of claim 1, wherein the oil is heated prior to contacting with the adsorbent.

6. The method of claim 1, wherein the heating step is performed at less than or equal to about 1 Torr.

7. The method of claim 1, wherein the heating step is performed at less than or equal to about 0.01 Torr.

8. The method of claim 1, wherein the mixture is mixed before, during, or after the heating step.

9. The method of claim 1, wherein the adsorbent further comprises silica.

10. The method of claim 1, wherein the adsorbent comprises silica and clay in a weight ratio of about 1:1.

11. The method of claim 1, wherein the oil comprises a marine oil.

12. The method of claim 1, wherein the oil comprises a fish oil.

13. The method of claim 1, wherein the oil comprises an Atlantic fish oil, Pacific fish oil, Mediterranean fish oil, light pressed fish oil, alkaline treated fish oil, heat treated fish oil, light and heavy brown fish oil, tuna oil, bonito oil, sea bass oil, halibut oil, spearfish oil, barracuda oil, cod oil, menhaden oil, sardine oil, pilchard oil, anchovy oil, capelin oil, Atlantic cod oil, Atlantic herring oil, Atlantic mackerel oil, Atlantic menhaden oil, salmonids oil, or combination thereof.

14. The method of claim 1, wherein the oil comprises a plant oil, animal oil, microbe oil, or edible oil.

15. The method of claim 1, wherein the oil comprises a crude oil, a semi-refined oil, a refined oil, or a re-esterified oil.

16. The method of claim 1, wherein the oil comprises a fish oil comprising an EPA to DHA wt. % ratio of about 18:12.

* * * * *